US006225315B1

(12) United States Patent
Ellis

(10) Patent No.: US 6,225,315 B1
(45) Date of Patent: May 1, 2001

(54) METHOD OF TREATING NITRATE-INDUCED TOLERANCE

(75) Inventor: Peter Ellis, Sandwich (GB)

(73) Assignee: Pfizer INC, New York, NY (US)

( * ) Notice: Subject to any disclaimer, the term of this patent is extended or adjusted under 35 U.S.C. 154(b) by 0 days.

(21) Appl. No.: 09/442,821

(22) Filed: Nov. 18, 1999

Related U.S. Application Data
(60) Provisional application No. 60/110,335, filed on Nov. 30, 1998.

(51) Int. Cl.[7] .................. A61K 31/495; A61K 31/505
(52) U.S. Cl. .................. 514/250; 514/258; 514/259
(58) Field of Search .................. 514/258, 259, 514/250

(56) References Cited

U.S. PATENT DOCUMENTS

| | | | |
|---|---|---|---|
| 5,250,534 | 10/1993 | Bell et al. | 514/258 |
| 5,272,147 | 12/1993 | Bell et al. | 514/234.2 |
| 5,294,612 | 3/1994 | Bacon et al. | 514/234.2 |
| 5,346,901 | 9/1994 | Bell et al. | 514/258 |
| 5,482,941 | 1/1996 | Terrett | 514/253 |
| 5,488,055 | 1/1996 | Kumar et al. | 514/293 |
| 5,541,187 | 7/1996 | Bacon et al. | 514/258 |
| 5,591,742 | 1/1997 | Bell et al. | 514/234.5 |
| 5,614,530 | 3/1997 | Kumar et al. | 514/293 |
| 5,656,629 | 8/1997 | Bacon et al. | 514/234.5 |
| 5,734,053 | 3/1998 | Terrett | 544/277 |
| 5,736,548 | 4/1998 | Bacon et al. | 514/258 |

FOREIGN PATENT DOCUMENTS

| | | |
|---|---|---|
| WO 9312095 | 6/1939 | (WO) . |
| WO 9306104 | 4/1993 | (WO) . |
| WO 9307149 | 4/1993 | (WO) . |
| WO 9400453 | 1/1994 | (WO) . |
| WO 9428902 | 12/1994 | (WO) . |
| WO 9628429 | 9/1996 | (WO) . |
| WO 9628446 | 9/1996 | (WO) . |
| WO 9628448 | 9/1996 | (WO) . |
| WO 9849166 | 11/1998 | (WO) . |

OTHER PUBLICATIONS

Anderson, T. L. G. et al. *Journal of Cardiovascular Pharmacology*, vol. 18 (2): pp. 237–242 (1991).
De Garavilla, L., et al. *Journal of Molecular and Cellular Cardiology*, vol. 24 (Suppl. 3): S37 (1992).
De Garavilla, L. et al. *European Journal of Pharmacology*, vol. 313 (1–2): pp. 89–96 (1996).
Merkel, L. A. et al. *European Journal of Pharmacology*, vol. 216 (1): pp. 29–35 (1992).
Pagani, E. D. et al. *European Journal of Pharmacology*, vol. 243 (2): pp. 141–147 (1993).
Saeki, T. et al. *Journal of Pharmacology and Experimental Therapeutics*, vol. 272 (2): pp. 825–831 (1995).
Silver, P. J. et al. *European Journal of Pharmacology*, vol. 199 (1): pp. 141–142 (1991).
Szilvassy, Z. et al. *Journal of Molecular and Cellular Cardiology*, vol. 28 (5): A97 (1996).
Thompson, W. J. et al. *Biochem.* 10:311 (1971).
Thompson, W. J. et al. *Biochem.* 18:5228 (1979).

*Primary Examiner*—Raymond Henley, III
(74) *Attorney, Agent, or Firm*—Peter C. Richardson; Gregg C. Benson; Jennifer A. Eispert

(57) ABSTRACT

The present invention relates to methods for treating nitrate-induced tolerance in a mammal by administering a nitrate-induced tolerance treating amount of a compound of formulae (I), (II), (III) (IV), (V), (VI), (VII), (VIII), (IX), (XA) or (XB) as defined herein, or the pharmaceutically acceptable salts, prodrugs, polymorphs, hydrates, solvates, active metabolites or stereoisomers thereof. The invention also relates to pharmaceutical compositions for the treatment of nitrate-induced tolerance in a mammal comprising a nitrate-induced tolerance treating amount of a compound of formulae (I), (II), (III) (IV), (V), (VI), (VII), (VIII), (IX), (XA) or (XB) as defined herein, or the pharmaceutically acceptable salts, prodrugs, polymorphs, hydrates, solvates, active metabolites or stereoisomers thereof, and a pharmaceutically acceptable vehicle, diluent or carrier. The invention further relates to methods of preventing nitrate-induced tolerance in a mammal comprising administering a nitrate-induced tolerance preventing amount of a cGMP PDE inhibitor.

42 Claims, No Drawings

METHOD OF TREATING NITRATE-INDUCED TOLERANCE

CROSSREFERENCE TO RELATED APPLICATION

This application claims priority from U.S. Provisional Patent Application No. 60/110,335 filed Nov. 30, 1998, the benefit of which is hereby claimed under 37 C.F.R. §1.78 (a)(3).

FIELD OF THE INVENTION

The present invention relates to the use of certain pyrazolo[4,3-d]pyrimidin-7-ones, pyrazolo[3,4-d] pyrimidin-4-ones, quinazolin-4-ones, purin-6-ones, pyrido [3,2-d]pyrimidin-4-ones and tetracyclic derivatives to treat nitrate-induced tolerance.

BACKGROUND OF THE INVENTION

Organic nitrate esters such as, for example, glyceryl trinitrate, commonly referred to as "nitroglycerin," are well known antihypertensive agents. Administration of organic nitrate esters results in, for example, the relaxation of vascular smooth muscle. Patients having hypertension, angina pectoris, congestive heart disease, myocardial infarction, peripheral vascular disease and airways diseases often receive ongoing nitrate therapy.

It is well known that the magnitude and duration of the desired activities of nitrates diminish on chronic, continuous dosing of nitrates. This diminished activity is commonly referred to as "nitrate tolerance." While nitrate tolerance can often be avoided or reduced by intermittent versus chronic, continuous dosing, undesirable events, e.g., "rebound angina," may occur during such nitrate-free periods.

Accordingly, nitrate-induced tolerance diminishes the efficacy of the nitrate therapy, and increased doses of organic nitrate esters are often administered to provide the desired therapeutic and pharmacological effects. Efforts have been made to reduce or reverse nitrate-induced tolerance by determining, for example, how the effects of organic nitrate esters are mediated on a cellular level.

On a cellular level, cyclic guanosine 3',5'-monophosphate ("cGMP") is thought to be the second messenger through which the vascular and other effects of organic nitrate esters are mediated. Briefly, cGMP is formed from guanosine 5'-triphosphate by the enzyme guanosine 5'-triphosphate pyrophosphate ("guanylate cyclase"). The termination of cGMP action is catalyzed by cyclic nucleotide phosphodiesterases ("PDEs") which cause the opening of a 3',5'-cyclic phosphoester bond yielding 5'-cGMP.

Organic nitrate esters are known to activate guanylate cyclase leading to increased cGMP levels, and tolerance to nitrates is associated with a reduced ability to generate cGMP. Nitrate-induced increased cGMP levels can be maintained either through less degradation of existing cGMP or by increased synthesis of cGMP. For example, inhibitors of cGMP-specific cyclic nucleotide PDEs can be used to block the termination of cGMP action by maintaining cGMP levels, e.g., provided by organic nitrate ester activation of guanylate cyclase.

Reversal of nitroglycerin tolerance in vitro by a cGMP PDE inhibitor, i.e., zaprinast (also known as "M&B 22,948"), has been described in articles by: P. J. Silver et al. published in the European Journal of Pharmacology, Vol. 199 (1): pp. 141–142 (1991), T. L. G. Anderson et al. published in the Journal of Cardiovascular Pharmacology, Vol. 18 (2): pp. 237–242 (1991), L. A. Merkel et al. published in the European Journal of Pharmacology, Vol. 216 (1): pp. 29–35 (1992), L. De Garavilla et al. published in the Journal of Molecular and Cellular Cardiology, Vol. 24 (Suppl. 3): S37 (1992) and in the European Journal of Pharmacology, Vol. 313 (1–2): pp. 89–96 (1996), and by E. D. Pagani et al. published in the European Journal of Pharmacology, Vol. 243 (2): pp. 141–7 (1993).

Synergism of a cGMP PDE inhibitor, i.e., E4021, with nitroglycerin, has been described in an article by T. Saeki et al. published in the Journal of Pharmacology and Experimental Therapeutics, Vol. 272 (2): pp. 825–831 (1995) (an increase in cGMP levels and a relaxant effect in isolated porcine coronary artery).

Reversal of nitroglycerin tolerance in vitro by a cGMP PDE inhibitor, i.e., cicletanine, has been described in an article by Z. Szilvassy et al. published in the Journal of Molecular and Cellular Cardiology, Vol. 28 (5): A97 (1996).

U.S. Pat. No. 5,294,612 discloses 6-heterocyclyl-pyrazolo [3,4-d]pyrimidin-4-ones possessing cGMP PDE I inhibitory activity, and the use of such compounds in combination with nitrates to reverse and/or reduce nitrate-induced tolerance.

U.S. Pat. No. 5,488,055 and International PCT Application published as WO 96/28446 disclose substituted N-cycloalkylmethyl-1H-pyrazolo[3,4-b]quinolin- 4-amines possessing c-GMP PDE V inhibitory activity, and the use of such compounds in combination with nitrates to reverse and/or reduce nitrate-induced tolerance.

U.S. Pat. No. 5,541,187, a division of the aforementioned U.S. Pat. No. 5,294,612, discloses 6-heterocyclyl-pyrazolo [3,4-d]pyrimidin-4-ones possessing cGMP PDE I inhibitory activity, and the use of such compounds in combination with nitrates to reverse and/or reduce nitrate-induced tolerance.

U.S. Pat. No. 5,614,530 and International PCT Application published as WO 96/128159 disclose substituted N-arylmethyl and heterocyclylmethyl-1H-pyrazolo[3,4-b] quinolin-4-amines possessing c-GMP PDE V inhibitory activity, and the use of such compounds in combination with nitrates to reverse and/or reduce nitrate-induced tolerance.

U.S. Pat. No. 5,656,629 and International PCT Application published as WO 96/28429 disclose 6-substituted pyrazolo[3,4-d]pyrimidin-4-one derivatives possessing c-GMP PDE V inhibitory activity, and the use of such compounds in combination with nitrates to reverse and/or reduce nitrate-induced tolerance.

U.S. Pat. No. 5,736,548 and International PCT Application published as WO 96/28448 disclose 6-arylpyrazolo[3, 4-d]pyrimidin-4-one derivatives possessing c-GMP PDE V inhibitory activity, and the use of such compounds in combination with nitrates to reverse and/or reduce nitrate-induced tolerance.

U.S. Pat. Nos. 5,250,534, 5,272,147, and 5,346,901, a division of the aforementioned U.S. Pat. No. 5,250,534, and International PCT Applications published as WO 93/06104, WO 93/07149, WO 94/28902 and WO 98/49166, disclose pyrazolo[4,3-d]pyrimidinones possessing cGMP PDE inhibitory activity.

U.S. Pat. No. 5,734,053 and International PCT Application published as WO 94/00453 disclose purinones possessing cGMP PDE inhibitory activity.

U.S. Pat. No. 5,482,941 and International PCT Application published as WO 93/12095 disclose quinazolinones possessing cGMP PDE inhibitory activity.

U.S. Pat. No. 5,591,742 and International PCT Application published as WO 94/05661 disclose pyridopyrimidinones possessing cGMP PDE inhibitory activity.

International PCT Application published as WO 96/16657 discloses 5-arylpyrazolo[4,3-d]pyrimidin-7-ones, 6-arylpyrazolo[3,4-d]pyrimidin-4-ones, 2-arylquinazolin-4-ones, 2-arylpurin-6-ones and 2-arylpyrido[3,2-d]pyrimidin-4-ones possessing cGMP PDE inhibitory activity.

International PCT Application published as WO 95/19978 discloses tetracyclic derivatives possessing cGMP PDE inhibitory activity. International PCT application published as WO 97/03675 discloses the use of such tetracyclic derivatives to treat impotence.

The present invention relates to the use of certain pyrazolo[4,3-d]pyrimidin-7-ones, pyrazolo[3,4-d]pyrimidin-4-ones, quinazolin-4-ones, purin-6-ones, pyrido[3,2-d]pyrimidin-4-ones and tetracyclic derivatives for the treatment of nitrate-induced tolerance.

All of the documents cited herein, including the foregoing, are incorporated by reference herein in their entireties.

SUMMARY OF THE INVENTION

The present invention relates to certain pyrazolo[4,3-d]pyrimidin-7-ones, pyrazolo[3,4-d]pyrimidin-4-ones, quinazolin-4-ones, purin-6-ones, pyrido[3,2d]pyrimidin-4-ones or tetracyclic derivatives, and the pharmaceutically acceptable salts, prodrugs, polymorphs, hydrates, solvates, active metabolites and stereoisomers thereof, which are useful in the treatment of nitrate-induced tolerance.

Specifically, suitable compounds include those which are disclosed in the aforementioned U.S. Pat. Nos. 5,250,534, 5,272,147, 5,346,901, 5,734,053, 5,482,941 and 5,591,742 and the International PCT Applications published as WO 93/06104, WO 93/07149, WO 93/12095, WO 94/00453, WO 94/05661, WO 94/28902, WO 96/16657, WO 95/19978; WO 97/03675; and WO 98/49166.

Thus, the present invention provides methods of treating nitrate-induced tolerance in a mammal which comprise administering to said mammal a nitrate-tolerance treating amount of a compound of formulae (I), (II), (III), (IV), (V), (VI), (VII), (VIII), (IX), (XA) or (XB) herein, or the pharmaceutically acceptable salts, prodrugs, polymorphs, hydrates, solvates, active metabolites or stereoisomers thereof.

Also provided by the present invention are pharmaceutical compositions for the treatment of nitrate-induced tolerance comprising a nitrate-induced tolerance treating amount of a compound of formulae (I), (II), (III), (IV), (V), (VI), (VII), (VIII), (IX), (XA) or (XB) herein, or the pharmaceutically acceptable salts, prodrugs, polymorphs, hydrates, solvates, active metabolites or stereoisomers thereof, and a pharmaceutically acceptable vehicle, diluent or carrier.

In a first aspect of the present invention the compound of the novel methods and pharmaceutical compositions for treating nitrate-induced tolerance is selected from those which are disclosed in the aforementioned U.S. Pat. No. 5,250,534, including, for example, the compounds of formula (I) below:

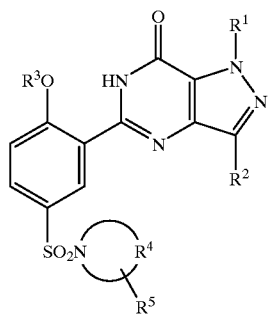

(I)

and the pharmaceutically acceptable salts, prodrugs, polymorphs, hydrates, solvates, active metabolites and stereoisomers thereof; wherein:

$R^1$ is H, $C_1$–$C_3$ alkyl, $C_3$–$C_5$ cycloalkyl or $C_1$–$C_3$ perfluoroalkyl;

$R^2$ is H, $C_1$–$C_6$ alkyl optionally substituted by OH, $C_1$–$C_3$ alkoxy or $C_3$–$C_6$ cycloalkyl, or $C_1$–$C_3$ perfluoroalkyl;

$R^3$ is $C_1$–$C_6$ alkyl, $C_3$–$C_6$ alkenyl, $C_3$–$C_6$ alkynyl, $C_3$–$C_7$ cycloalkyl, $C_1$–$C_6$ perfluoroalkyl or ($C_3$–$C_6$ cycloalkyl) $C_1$–$C_6$ alkyl;

$R^4$ taken together with the nitrogen atom to which it is attached completes a 4-N—($R^6$)-piperazinyl group;

$R^5$ is H, $C_1$–$C_4$ alkyl, $C_1$–$C_3$ alkoxy, $NR^7R^8$ or $CONR^7R^8$;

$R^6$ is H, $C_1$–$C_6$ alkyl, ($C_1$–$C_3$ alkoxy)$C_2$–$C_6$ alkyl, hydroxy $C_2$–$C_6$ alkyl, ($R^7R^8N$)$C_2$–$C_6$ alkyl, ($R^7R^8NCO$)$C_1$–$C_6$ alkyl, $CONR^7R^8$, $CSNR^7R^8$ or $C(NH)NR^7R^8$; and $R^7$ and $R^8$ are each independently H, $C_1$–$C_4$alkyl, ($C_1$–$C_3$ alkoxy)$C_2$–$C_4$ alkyl or hydroxy $C_2$–$C_4$ alkyl.

In a second aspect of the present invention the compound of the novel methods and pharmaceutical compositions for treating nitrate-induced tolerance is selected from those which are disclosed in the aforementioned U.S. Pat. No. 5,272,147 including, for example, the compounds of formula (II) below:

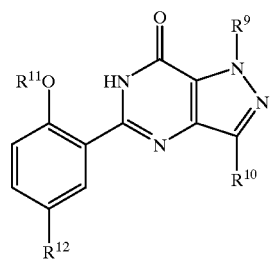

(II)

and the pharmaceutically acceptable salts, prodrugs, polymorphs, hydrates, solvates, active metabolites and stereoisomers thereof; wherein:

$R^9$ is H, $C_1$–$C_3$ alkyl optionally substituted with one or more fluoro substituents, or $C_3$–$C_5$ cycloalkyl;

$R^{10}$ is H or $C_1$–$C_6$ alkyl optionally substituted with one or more fluoro substituents or with $C_3$–$C_6$ cycloalkyl;

$R^{11}$ is $C_1$–$C_6$ alkyl optionally substituted with one or more fluoro substituents or with $C_3$–$C_6$ cycloalkyl, or $C_3$–$C_5$ cycloalkyl, or $C_3$–$C_6$ alkenyl, or $C_3$–$C_6$ alkynyl;

$R^{12}$ is $C_1$–$C_4$ alkyl optionally substituted with OH, $NR^{13}R^{14}$, CN, $CONR^{13}R^{14}$ or with $CO_2R^{15}$, or $C_2$–$C_4$ alkenyl optionally substituted with CN, CONR$^{13}$R$^{14}$ or with CO$_2$R$^{15}$, or C$_2$–C$_4$ alkanoyl optionally substituted with NR$^{13}$R$^{14}$, or hydroxy C$_2$–C$_4$ alky optionally substituted with NR$^{13}$R$^{14}$, or (C$_2$–C$_3$ alkoxy)C$_1$–C$_2$ alkyl optionally substituted with OH or NR$^{13}$R$^{14}$, or CONR$^{13}$R$^{14}$, or CO$_2$R$^{15}$, or halo, or NR$^{13}$R$^{14}$, or NHSO$_2$NR$^{13}$R$^{14}$, or NHSO$_2$R$^{16}$, or phenyl or heterocyclyl either of which is optionally substituted with methyl;

R$^{13}$ and R$^{14}$ are each independently H, C$_1$–C$_4$ alkyl, or together with the nitrogen atom to which they are attached form a pyrrolidinyl, piperidino, morpholino, 4-(NR$^{17}$)-piperazinyl or imidazolyl group wherein said group is optionally substituted with methyl or hydroxy;

R$^{15}$ is H or C$_1$–C$_4$ alkyl;

R$^{16}$ is C$_1$–C$_3$ alkyl optionally substituted with NR$^{13}$R$^{14}$; and R$^{17}$ is H, C$_1$–C$_3$ alkyl optionally substituted with phenyl, or hydroxy C$_2$–C$_3$ alkyl, or C$_1$–C$_4$ alkanoyl.

In a third aspect of the present invention the compound of the novel methods and pharmaceutical compositions for treating nitrate-induced tolerance is selected from those which are disclosed in the aforementioned U.S. Pat. No. 5,346,901 including, for example, the compounds of formula (III) below:

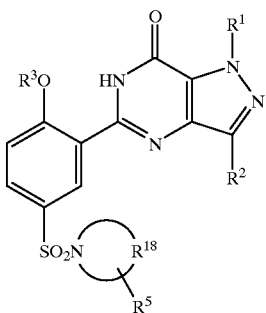

(III)

and the pharmaceutically acceptable salts, prodrugs, polymorphs, hydrates, solvates, active metabolites and stereoisomers thereof; wherein: R$^4$, R$^2$, R$^3$ and R$^5$ are as previously described for formula (I) herein, and R$^{18}$ taken together with the nitrogen to which it is attached completes a pyrrolidinyl, piperidino or morpholino group.

In a fourth aspect of the present invention the compound of the novel methods and pharmaceutical compositions for treating nitrate-induced tolerance is selected from those which are disclosed in the aforementioned U.S. Pat. No. 5,734,053 and International PCT Application published as WO 94/00453, including, for example, the compounds of formula (IV) below:

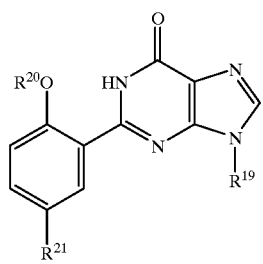

(IV)

and the pharmaceutically acceptable salts, prodrugs, polymorphs, hydrates, solvates, active metabolites and stereoisomers thereof; wherein:

R$^{19}$ is C$_1$–C$_4$ alkyl;

R$^{20}$ is C$_2$–C$_4$ alkyl;

R$^{21}$ is H or SO$_2$NR$^{22}$R$^{23}$;

R$^{22}$ and R$^{23}$ together with the nitrogen atom to which they are attached form a pyrrolidino, piperidino, morpholino or 4-N—(R$^{24}$)-1-piperazinyl group; and R$^{24}$ is H or C$_1$–C$_3$ alkyl.

In a fifth aspect of the present invention the compound of the novel methods and pharmaceutical compositions for treating nitrate-induced tolerance is selected from those which are disclosed in the aforementioned U.S. Pat. No. 5,482,941 and International PCT Application published as WO 93/12095, including, for example, the compounds of formula (V) below:

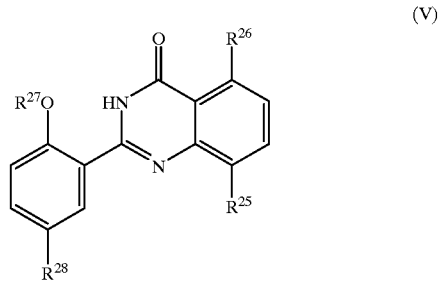

(V)

and the pharmaceutically acceptable salts, prodrugs, polymorphs, hydrates, solvates, active metabolites and stereoisomers thereof; wherein:

R$^{25}$ is H, C$_1$–C$_4$ alkyl, C$_1$–C$_4$ alkoxy or CONR$^{29}$R$^{30}$;

R$^{26}$ is H or C$_1$–C$_4$ alkyl;

R$^{27}$ is C$_2$–C$_4$ alkyl;

R$^{28}$ is H, C$_2$–C$_4$ alkanoyl optionally substituted with NR$^{31}$R$^{32}$, or (hydroxy)C$_2$–C$_4$ alkyl optionally substituted with NR$^{31}$R$^{32}$, or CH=CHCO$_2$R$^{33}$, or CH=CHCONR$^{31}$R$^{32}$, or CH$_2$CH$_2$CO$_2$R$^{33}$, or CH$_2$CH$_2$CONR$^{31}$R$^{32}$, or SO$_2$NR$^{31}$R$^{32}$, or SO$_2$NH(CH$_2$)$_n$NR$^{31}$R$^{32}$ or imidazolyl;

R$^{29}$ and R$^{30}$ are each independently H or C$_1$–C$_4$ alkyl;

R$^{31}$ and R$^{32}$ are each independently H or C$_1$–C$_4$ alkyl, or together with the nitrogen atom to which they are attached form a pyrrolidino, piperidino, morpholino or 4-(NR$^{34}$)-1-piperazinyl group wherein any of said groups is optionally substituted with CONR$^{29}$R$^{30}$;

R$^{33}$ is H or C$_1$–C$_4$ alkyl;

R$^{34}$ is H, C$_1$–C$_3$ alkyl or (hydroxy)C$_2$–C$_3$ alkyl; and n is 2, 3 or 4; and provided that R$^{28}$ is not H when R$^{25}$ is H, C$_1$–C$_4$ alkyl or C$_1$–C$_4$ alkoxy.

In a sixth aspect of the present invention the compound of the novel methods and pharmaceutical compositions for treating nitrate-induced tolerance is selected from those which are disclosed in the aforementioned U.S. Pat. No. 5,591,742 and International PCT Application published as WO 94/05661, including, for example, the compounds of formula (VI) below:

(VI)

and the pharmaceutically acceptable salts, prodrugs, polymorphs, hydrates, solvates, active metabolites and stereoisomers thereof; wherein:

$R^{35}$ is H, $C_1$–$C_4$ alkyl, CN or $CONR^{29}R^{30}$;

$R^{36}$ is $C_2$–$C_4$ alkyl;

$R^{37}$ is $SO_2NR^{38}R^{39}$, $NO_2$, $NH_2$, $NHCOR^{42}$, $NHSO_2R^{42}$ or $N(SO_2R^{42})_2$;

$R^{38}$ and $R^{39}$ are each independently selected from H and $C_1$–$C_4$ alkyl optionally substituted with $CO_2R^{43}$, OH, pyridyl, 5-isoxazolin-3-onyl, morpholino or 1-imidazolidin-2-onyl, or together with the nitrogen atom to which they are attached form a pyrrolidino, piperidino, morpholino, 1-pyrazolyl or 4-($NR^{44}$)-1-piperazinyl group wherein any of said groups may optionally be substituted with one or two substituents selected from $C_1$–$C_4$ alkyl, $CO_2R^{43}$, $NH_2$ and OH;

$R^{42}$ is $C_1$–$C_4$ alkyl or pyridyl;

$R^{43}$ is H or $C_1$–$C_4$ alkyl; and $R^{44}$ is H, $C_1$–$C_4$ alkyl or (hydroxy)$C_2$–$C_3$ alkyl.

In a seventh aspect of the present invention the compound of the novel methods and pharmaceutical compositions for treating nitrate-induced tolerance is selected from those which are disclosed in the aforementioned International PCT Application published as WO 93/07149, including, for example, the compounds of formula (VII) below:

(VII)

and the pharmaceutically acceptable salts, prodrugs, polymorphs, hydrates, solvates, active metabolites and stereoisomers thereof; wherein:

$R^{45}$ is $C_1$–$C_6$ alkyl;

$R^{46}$ is H, methyl or ethyl;

$R^{47}$ is $C_2$–$C_4$ alkyl;

$R^{48}$ is $C_1$–$C_4$ alkyl optionally substituted with $NR^{49}R^{50}$, CN, $CONR^{49}R^{50}$ or $CO_2R^{51}$; $C_2$–$C_4$ alkenyl optionally substituted with CN, $CONR^{49}R^{50}$ or $CO_2R^{51}$; $C_2$–$C_4$ alkanoyl optionally substituted with $NR^{49}R^{50}$; $SO_2NR^{49}R^{50}$; $CONR^{49}R^{50}$; $CO_2R^{51}$; or halo;

$R^{49}$ and $R^{50}$ are each independently H or $C_1$–$C_4$ alkyl, or together with the nitrogen atom to which they are attached form a pyrrolidino, piperidino, morpholino, 4-($NR^{52}$)-1-piperazinyl or 1-imidazolyl group wherein said group is optionally substituted by one or two $C_1$–$C_4$ alkyl groups;

$R^{51}$ is H or $C_1$–$C_4$ alkyl; and $R^{52}$ is H, $C_1$–$C_3$ alkyl or hydroxy $C_2$–$C_3$ alkyl.

In an eighth aspect of the present invention the compound of the novel methods and pharmaceutical compositions for treating nitrate-induced tolerance is selected from those which are disclosed in the aforementioned International PCT Application published as WO 93/06104, including, for example, the compounds of formula (VIII) below:

(VIII)

and the pharmaceutically acceptable salts, prodrugs, polymorphs, hydrates, solvates, active metabolites and stereoisomers thereof; wherein:

$R^{53}$ is methyl or ethyl;

$R^{54}$ is ethyl or n-propyl;

$R^{55}$ and $R^{56}$ are each independently H or $C_1$–$C_6$ alkyl optionally substituted with $C_5$–$C_7$ cycloalkyl or with morpholino.

In a ninth aspect of the present invention the compound of the novel methods and pharmaceutical compositions for treating nitrate-induced tolerance is selected from those which are disclosed in the aforementioned International PCT Applications published as WO 95/19978 and WO 97/03675, including, for example, the compounds of formula (IX) below:

(IX)

and the pharmaceutically acceptable salts, prodrugs, polymorphs, hydrates, solvates, active metabolites and stereoisomers thereof; wherein:

$R^{57}$ is hydrogen, halogen or $C_{1-6}$ alkyl;

$R^{58}$ is hydrogen, $C_{1-6}$ alkyl, $C_{2-6}$ alkenyl, $C_{2-6}$ alkynyl, halo $C_{1-6}$ alkyl, $C_{3-8}$ cycloalkyl, $C_{3-8}$ cycloalkyl $C_{1-3}$ alkyl, aryl, aryl $C_{1-3}$ alkyl or heteroaryl $C_{1-3}$ alkyl;

$R^{59}$ is an optionally substituted monocyclic aromatic ring selected from benzene, thiophene, furan and pyridine or an optionally substituted bicyclic ring

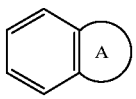

attached to the rest of the molecule via one of the benzene ring carbon atoms and wherein the fused ring A is a 5- or 6-membered ring which may be saturated or partially or fully unsaturated and comprises carbon atoms and optionally one or two heteroatoms selected from oxygen, sulfur and nitrogen; and $R^{60}$ is hydrogen or $C_{1-3}$ alkyl, or $R^{58}$ and $R^{60}$ together represent a 3- or 4-membered alkyl or alkenyl chain.

In a tenth aspect of the present invention the compound of the novel methods and pharmaceutical compositions for treating nitrate-induced tolerance is selected from those which are disclosed in the aforementioned International PCT Application published as WO 98/49166 including, for example, the compounds of formulae (XA) and (XB) below:

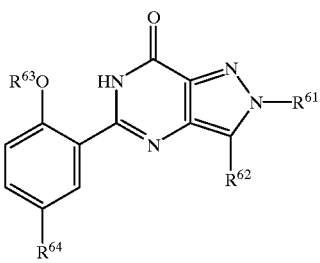

(XA)

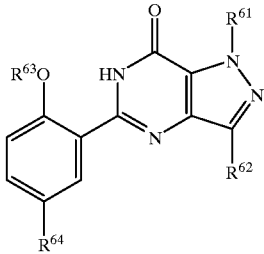

(XB)

and the pharmaceutically acceptable salts, prodrugs, polymorphs, hydrates, solvates, active metabolites and stereoisomers thereof; wherein:

$R^{61}$ is $C_1$–$C_3$ alkyl substituted with $C_3$–$C_6$ cycloalkyl, $CONR^{55}R^{66}$ or a N-linked heterocyclic group selected from pyrazolyl, imidazolyl, triazolyl, pyrrolidinyl, piperidinyl, morpholinyl and 4-$R^{67}$-piperazinyl; $(CH_2)_p$Het or $(CH_2)_q$Ar;

$R^{62}$ is $C_1$–$C_6$ alkyl;

$R^{63}$ is $C_1$–$C_6$ alkyl optionally substituted with $C_1$–$C_4$ alkoxy;

$R^{64}$ is $SO_2NR^{68}R^{69}$;

$R^{65}$ and $R^{66}$ are each independently selected from H and $C_1$–$C_4$ alkyl optionally substituted with $C_1$–$C_4$ alkoxy, or, together with the nitrogen atom to which they are attached, form a pyrrolidinyl, piperidinyl, morpholinyl or 4-$R^{67}$-piperazinyl group;

$R^{68}$ and $R^{69}$, together with the nitrogen atom to which they are attached, form a 4-$R^{70}$-piperazinyl group;

$R^{67}$ is $C_1$–$C_4$ alkyl;

$R^{70}$ is H or $C_1$–$C_4$ alkyl optionally substituted with OH, $C_1$–$C_4$ alkoxy or $CONH_2$;

Het is a C-linked 6-membered heterocyclic group containing one or two nitrogen atoms, optionally in the form of its mono-N-oxide, or a C-linked 5-membered ring heterocyclic group containing from one to four heteroatoms selected from nitrogen, oxygen and sulfur, wherein either of said heterocyclic groups is optionally substituted with one or two substituents selected from $C_1$–$C_4$ alkyl optionally substituted with $C_1$–$C_4$ alkoxy, $C_1$–$C_4$ alkoxy, halo and $NH_2$;

Ar is phenyl optionally substituted with one or two substituents selected from $C_1$–$C_4$ alkyl, $C_1$–$C_4$ alkoxy, halo, CN, $CONH_2$, $NO_2$, $NH_2$, $NHSO_2$ ($C_1$–$C_4$ alkyl) and $SO_2NH_2$; and p and q are each independently 0 or 1.

In an eleventh aspect, the present invention provides a method for preventing nitrate-induced tolerance in a mammal comprising administering to such mammal a nitrate-induced tolerance preventing amount of a cGMP PDE inhibitor.

Any suitable nitric oxide inhibitor, e.g., organic nitrate, i.e., polyol ester of nitric acid (—C—O—$NO_2$), may be used in the novel methods of the present invention. Suitable organic nitrates include, for example, those of low, e.g., glyceryl trinitrate, and high, e.g., erythrityl tetranitrate, pentaerythritol tetranitrate and isosorbide dinitrate, molecular mass. Preferred organic nitrates include glyceryl trinitrate.

DETAILED DESCRIPTION OF THE INVENTION

Those skilled in the art will fully understand the terms used herein to describe the compounds comprising the novel methods and pharmaceutical compositions; nonetheless, the following terms used herein, unless otherwise provided by the aforementioned U.S. Pat. Nos. 5,250,534; 5,272,147; 5,346,901; 5,734,053; 5,482,941; and 5,591,742, and the International PCT Applications published as WO 93/06104; WO 93/07149; WO 93/12095; WO 94/00453; WO 94/05661; WO 94/28902; WO 96/16657; WO 95/19978; WO 97/03675 and WO 98/49166, are as described below.

"Alkanoyl" means a univalent or bivalent acyl radical formed by removal of hydroxyl from the carboxyl group which replaced the methyl group at the end of the main chain of the acyclic hydrocarbon.

"Alkenyl" means an unsaturated, unbranched acyclic hydrocarbon radical having one double bond.

"Alkoxy" means an alkyl radical attached to the remainder of the molecule by oxygen, including, for example, methoxy.

"Alkyl" means a straight or branched hydrocarbon chain radical, including, for example, methyl, ethyl, n-propyl, isopropyl, n-butyl and the like.

"Alkynyl" means an unsaturated, unbranched acyclic hydrocarbon radical having one triple bond, including, for example, acetylene.

"Allyl" means prop-2-enyl, i.e., the radical —$CH_2CH=CH_2$.

"Aryl" means an organic radical derived from an aromatic hydrocarbon by the removal of one atom, e.g., phenyl from benzene, also including, for example, naphthyl.

"Cycloalkane" means a saturated, monocyclic hydrocarbon, including, for example, cyclohexane.

"Cycloalkyl" means a monocyclic or polycyclic radical derived from a cycloalkane, including, for example, cyclohexyl, cyclobutyl, cyclopentyl and cycloheptyl.

"Halo" or "halogen" means a radical derived from the elements fluorine, chlorine, bromine and iodine.

"Heterocyclyl" means a radical derived from a ring of different types of atoms, and includes aromatic and non-aromatic heterocyclic groups containing one or more heteroatoms each selected from O, S and N. The heterocyclic groups include benzofused ring systems and ring systems substituted with an oxo moiety, e.g., benzimidazolyl, benzofuranyl, benzothiophenyl, benzoxazolyl, furyl, imidazolyl, indolyl, isoquinolyl, isothiazolyl, isoxazolyl, morpholinyl, oxadiazolyl, oxazolyl, piperazinyl, piperidyl, pyrazinyl, pyrazolyl, pyridyl, pyrimidyl, pyrrolyl, quinolyl, tetrahydroisoquinoly, tetrahydroquinolyl, tetrahydrothienyl, tetrazolyl, thiadiazolyl, thiazolyl, thienyl, thiomorpholinyl and triazolyl. Where heterocyclic groups are specifically recited or covered as substituents for the compounds of formulae (I)–(XB), it is understood that all suitable isomers of such heterocyclic groups are intended.

"Perfluoroalkyl" means that all of the H atoms, except those whose replacement would affect the nature of the characteristic groups present, are replaced with fluorine atoms, e.g., perfluoropentyl, $CF_3(CF_2)_3CF_2$—.

"Pharmaceutically acceptable salt(s)" includes salts of acidic or basic groups which may be present in the compounds suitable for use in the present invention, e.g., the compounds of formulae (I)–(XB) herein. For example, pharmaceutically acceptable salts include sodium, calcium and potassium salts of carboxylic acid groups and hydrochloride salts of amino groups. Other pharmaceutically acceptable salts of amino groups are hydrobromide, sulfate, hydrogen sulfate, phosphate, hydrogen phosphate, dihydrogen phosphate, acetate, succinate, citrate, tartrate, lactate, mandelate, methanesulfonate (mesylate) and p-toluenesulfonate (tosylate) salts. A preferred salt is the citrate.

"Treating," "treat" or "treatment" includes, inter alia, preventative (e.g., prophylactic), palliative and curative treatment, including, for example, the prevention, reduction and reversal of nitrate-induced tolerance.

As disclosed herein, a compound within the scope of formulae (I)–(XB), shall at all times be understood to include all active forms of such compounds, including, for example, the free form thereof, e.g., the free acid or base form and also, all pharmaceutically acceptable salts as described above, prodrugs, polymorphs, hydrates, solvates, stereoisomers, e.g., diastereomers and enantiomers, and the like. It will also be appreciated that active metabolites of compounds within the scope of formulae (I)–(XB), in any suitable form, are also included herein.

More specifically, certain compounds suitable for use in the present invention such as, for example, certain compounds of formulae (I)–(XB), may have asymmetric centers and therefore exist in different enantiomeric forms. All optical isomers and stereoisomers of such compounds, and mixtures thereof, are considered to be within the scope of the invention. With respect to such compounds, the present invention includes the use of a racemate, a single enantiomeric form, a single diastereomeric form, or mixtures thereof. Moreover, such compounds may also exist as tautomers. Accordingly, the present invention relates to the use of all such tautomers and mixtures thereof. Any suitable combination of any of the compounds of formulae (I)–(XB) herein, or the pharmaceutically acceptable salts, prodrugs, polymorphs, hydrates, solvates, active metabolites or stereoisomers thereof, may be used in the methods and pharmaceutical compositions of the present invention.

The preparation of the compounds suitable for use in the present invention including the compounds of formulae (I)–(XB) herein, and their pharmaceutically acceptable salts, and the preferred compounds thereof, pharmaceutical compositions thereof and routes of administration for mammalian use, can be understood and carried out by one skilled in the art in any suitable manner, e.g., according to one or more of the synthetic methods outlined in the synthetic schemes and examples described in considerable detail in the aforementioned U.S. Pat. Nos. 5,250,534; 5,272,147; 5,346,901; 5,734,053; 5,482,941 and 5,591,742, and the International PCT Applications published as WO 93/06104; WO 93/07149; WO 93/12095; WO 94/00453; WO 94/05661; WO 94/28902; WO 96/16657; WO 95/19978; WO 97/03675; and WO 98/49166.

Preferred compounds of formula (I) include those wherein $R^1$ is H, methyl or ethyl; $R^2$ is $C_1$–$C_3$ alkyl optionally substituted by OH or methoxy; $R^3$ is $C_2$–$C_3$ alkyl or allyl; $R^4$ taken together with the nitrogen atom to which it is attached completes a piperidino or 4-N—($R^6$)-piperazinyl group; $R^5$ is H, $NR^7R^8$ or $CONR^7R^8$; $R^6$ is H, $C_1$–$C_3$ alkyl, hydroxy $C_2$–$C_3$ alkyl, $CONR^7R^8$, $CSNR^7R^8$ or $C(NH)NR^7R^8$; and $R^7$ and $R^8$ are each independently H or methyl.

Other preferred compounds of formula (I) include those wherein $R^1$ is methyl; $R^2$ is n-propyl; $R^3$ is ethyl, n-propyl or allyl; $R^4$ taken together with the nitrogen atom to which it is attached completes a 4-N—($R^6$)-piperazinyl group; $R^5$ is H; $R^6$ is H, $C_1$–$C_3$ alkyl or 2-hydroxyethyl; and $R^7$ and $R^8$ are each independently H or methyl.

A further preferred compound of formula (I) is wherein $R^1$ is methyl, $R^2$ is n-propyl, $R^3$ is ethyl, $R^4$ taken together with the nitrogen atom to which it is attached completes a 4-N—($R^6$)-piperazinyl group, $R^5$ is hydrogen and $R^6$ is methyl.

Also preferred is the citrate salt of a compound of formula (I) wherein $R^1$ is methyl, $R^2$ is n-propyl, $R^3$ is ethyl, $R^4$ taken together with the nitrogen atom to which it is attached completes a 4-N—($R^6$)-piperazinyl group, $R^5$ is hydrogen and $R^6$ is methyl.

Preferred individual compounds of formula (I) include:
5-[2-allyloxy-5-(4-methylpiperazinylsulphonyl)phenyl]-1-methyl-3-n-propyl-1,6-dihydro-7H-pyrazolo[4,3-d]pyrimidin-7-one;

5-[2-ethoxy-5-(piperazinylsulphonyl)phenyl]-1-methyl-3-n-propyl-1,6-dihydro-7H-pyrazolo[4,3-d]pyrimidin-7-one;

5-[2-ethoxy-5-(4-methylpiperazinylsulphonyl)phenyl]-1-methyl-3-n-propyl-1,6-dihydro-7H-pyrazolo[4,3-d]pyrimidin-7-one;

5-{2-ethoxy-5-[4-(2-propyl)piperazinylsulphonyl]phenyl}-1-methyl-3-n-propyl-1,6-dihydro-7H-pyrazolo[4,3-d]pyrimidin-7-one;

5-{2-ethoxy-5-[4-(2-hydroxyethyl)piperazinylsulphonyl]phenyl}-1-methyl-3-n-propyl-1,6-dihydro-7H-pyrazolo[4,3-d]pyrimidin-7-one;

1-methyl-5-[5-piperazinylsulphonyl)-2-n-propoxyphenyl]-3-n-propyl-1,6-dihydro-7H-pyrazolo[4,3-d]pyrimidin-7-one; and 5-{5-[4-(2-hydroxyethyl)piperazinyisulphonyl]-2-n-propoxyphenyl}-1-methyl-3-n-propyl-1,6-dihydro-7H-pyrazolo[4,3-d]pyrimidin-7-one.

Preferred compounds of formula (II) include those wherein $R^9$ is H, methyl or ethyl; $R^{10}$ is $C_1$–$C_3$ alkyl; $R^{11}$ is $C_2$–$C_3$ alkyl; $R^{12}$ is $C_1$–$C_2$ alkyl optionally substituted with OH, $NR^{13}R^{14}$, $CONR^{13}R^{14}$ or with $CO_2R^{15}$, acetyl optionally substituted with $NR^{13}R^{14}$, or hydroxyethyl substituted with $NR^{13}R^{14}$, or ethoxymethyl optionally substituted with OH or with $NR^{13}R^{14}$, or CH=CHCN, or CH=CHCONR$^{13}R^{14}$, or CH=CHCO$_2R^{15}$, or CO$_2$H, or CONR$^{13}R^{14}$, or Br, or $NR^{13}R^{14}$, or NHSO$_2NR^{13}R^{14}$, or NHSO$_2R^{16}$, or pyridinyl or imidazolyl either of which is optionally substituted with methyl; $R^{13}$ and $R^{14}$ are each independently H, methyl or ethyl, or together with the nitrogen atom to which they are attached form a piperidino, morpholino, 4-($NR^{17}$)-1-piperazinyl or imidazolyl group wherein said group is optionally substituted with methyl or hydroxy; $R^{15}$ is H or t-butyl; $R^{16}$ is methyl or CH$_2$CH$_2$CH$_2NR^{13}R^{14}$; and $R^{17}$ is H, methyl, benzyl, 2-hydroxyethyl or acetyl.

Other preferred compounds of formula (II) include those wherein $R^9$ is methyl; $R^{10}$ is n-propyl; $R^{11}$ is ethyl or n-propyl; $R^{12}$ is CH$_2NR^{13}R^{14}$, CH$_2$OCH$_2$CH$_2NR^{13}R^{14}$, CH$_2$OCH$_2$CH$_3$, CH$_2$OCH$_2$CH$_2$OH, COCH$_2NR^{13}R^{14}$, CH(OH)CH$_2NR^{13}R^{14}$, CH=CHCON(CH$_3$)$_2$, CH=CHCO$_2R^{15}$, CO$_2$H, CONR$^{13}R^{14}$, Br, NHSO$_2NR^{13}R^{14}$, NHSO$_2$CH$_2$CH$_2NR^{13}R^{14}$, 2-pyridyl, 1-imidazolyl or 1-methyl-2-imidazolyl; $R^{13}$ and $R^{14}$ together with the nitrogen atom to which they are attached form a piperidino, 4-hydroxypiperidino, morpholino, 4-($NR^{17}$)-1-piperazinyl or 2-methyl-1-imidazolyl group; $R^{15}$ is H or t-butyl; $R^{16}$ is methyl or CH$_2$CH$_2$CH$_2NR^{13}R^{14}$; and $R^{17}$ is H, methyl, benzyl, 2-hydroxyethyl or acetyl.

Preferred individual compounds of formula (II) include:

5-[2-ethoxy-5-(1-methyl-2-imidazolyl)phenyl]-1-methyl-3-n-propyl-1,6-dihydro-7H-pyrazolo[4,3-d]pyrimidin-7-one;

5-[2-ethoxy-5-(4-methyl-1-piperazinylcarbonyl)phenyl]-1-methyl-3-n-propyl-1,6-dihydro-7H-pyrazolo[4,3-d]pyrimidin-7-one;

5-[5-(4-acetyl-1-piperazinyl)acetyl-2-ethoxyphenyl]-1-methyl-3-n-propyl-1,6-dihydro-7H-pyrazolo[4,3-d]pyrimidin-7-one;

5-(2-ethoxy-5-morpholinoacetylphenyl)-1-methyl-3-n-propyl-1,6-dihydro-7H-pyrazolo[4,3-d]pyrimidin-7-one; and 5-(5-morpholinoacetyl-2-propoxyphenyl)-1-methyl-3-n-propyl-1,6-dihydro-7H-pyrazolo[4,3-d]pyrimidin-7-one.

Preferred compounds of formula (III) include those wherein $R^4$ is H, methyl or ethyl; $R^2$ is $C_1$–$C_3$ alkyl optionally substituted by OH or methoxy; $R^3$ is $C_2$–$C_3$ alkyl or allyl; $R^{18}$ taken together with the nitrogen atom to which it is attached completes a piperidino group; $R^5$ is H, $NR^7R^8$ or $CONR^7R^8$; and $R^7$ and $R^8$ are each independently H or methyl.

Preferred compounds of formula (IV) include those wherein $R^{19}$ and $R^{20}$ are each independently ethyl or n-propyl; and $R^{22}$ and $R^{23}$ together with the nitrogen atom to which they are attached form a 4-N—($R^{24}$)-1-piperazinyl group.

Other preferred compounds of formula (IV) include those wherein $R^{19}$ is n-propyl; $R^{20}$ is ethyl; and $R^{21}$ is 1-piperazinylsulphonyl or 4-methyl-1-piperazinylsulfonyl.

Preferred compounds of formula (V) include those wherein $R^{25}$ is H, methoxy or $CONR^{29}R^{30}$; $R^{26}$ is H or methyl; $R^{27}$ is ethyl or n-propyl; $R^{28}$ is H, acetyl optionally substituted with $NR^{31}R^{32}$, or hydroxyethyl substituted with $NR^{31}R^{32}$, or CH=CHCO$_2R^{32}$, or CH=CHCONR$^{31}R^{32}$, or CH$_2$CH$_2$CO$_2R^{33}$, or SO$_2NR^{31}R^{32}$, or SO$_2$NH(CH$_2$)$_3NR^{31}R^{32}$ or 1-imidazolyl; $R^{29}$ and $R^{30}$ are each independently H or ethyl; $R^{31}$ and $R^{32}$ together with the nitrogen atom to which they are attached form a piperidino, 4-carbamoylpiperidino, morpholino or 4-($NR^{34}$)-1-piperazinyl group; $R^{33}$ is H or t-butyl; and $R^{34}$ is H, methyl or 2-hydroxyethyl; provided that $R^{28}$ is not H when $R^{25}$ is H, methyl or methoxy.

Other preferred compounds of formula (V) include those wherein $R^{25}$ is methyl, CONH$_2$ or CONHCH$_2$CH$_3$; $R^{26}$ is H; $R^{27}$ is ethyl or n-propyl; $R^{28}$ is H, acetyl, 1-hydroxy-2-($NR^{31}R^{32}$)ethyl, CH=CHCO$_2$C(CH$_3$)$_3$, or CH=CHCONR$^{31}R^{32}$, or SO$_2NR^{31}R^{32}$ or 1-imidazolyl; $R^{31}$ and $R^{32}$ together with the nitrogen atom to which they are attached form a 4-($NR^{34}$)-1-piperazinyl group; and $R^{34}$ is methyl or 2-hydroxyethyl; provided that $R^{28}$ is not H when $R^{25}$ is methyl.

Preferred individual compounds of formula (V) include:

2-{2-ethoxy-5-[4-(2-hydroxyethyl)-1-piperazinylsulfonyl]phenyl}-8-methyl quinazolin-4(3H)-one;

2-{5-[4-(2-hydroxyethyl)-1-piperazinylsulfonyl]2-n-propoxyphenyl}-8-methyl quinazolin-4(3H)-one;

8-methyl-2-{5-[2-(4-methyl-1-piperazinylcarbonyl)ethenyl]-2-n-propoxy-phenyl}quinazolin-4(3H)-one;

8-carbamoyl-2-{2-ethoxy-5-[4-(2-hydroxyethyl)-1-piperazinylsulfonyl]phenyl}quinazolin-4(3H)-one; and 8-ethylcarbamoyl-2-(2-n-propoxyphenyl)quinazolin-4(3H)-one.

Preferred compounds of formula (VI) include those wherein $R^{35}$ is H, n-propyl, CN or CONH$_2$; $R^{36}$ is ethyl; $R^{37}$ is $SO_2NR^{40}R^{41}$, NO$_2$, NH$_2$, NHCOCH(CH$_3$)$_2$, NHSO$_2$CH(CH$_3$)$_2$, NHSO$_2$(3-pyridyl) or N[SO$_2$(3-pyridyl)]$_2$; $R^{40}$ is H, methyl or 2-hydroxyethyl; $R^{41}$ is methyl optionally substituted with 2-pyridyl or 5-isoxazolin-3-onyl, or ethyl 2-substituted with OH, CO$_2$CH$_2$CH$_3$, morpholino or with 1-imidazolidin-2-onyl; or $R^{40}$ and $R^{41}$ together with the nitrogen atom to which they are attached form a (4-CO$_2R^{43}$) piperidino, 5-amino-3-hydroxy-1-pyrazolyl or 4-($NR^{44}$)-1-piperazinyl group; $R^{43}$ is H or ethyl; and $R^{44}$ is H, methyl or 2-hydroxyethyl.

Other preferred compounds of formula (VI) include those wherein $R^{35}$ is n-propyl or CN; $R^{36}$ is ethyl; $R^{37}$ is $SO_2NR^{40}R^{41}$, NHSO$_2$CH(CH$_3$)$_2$, NHSO$_2$(3-pyridyl) or N[SO$_2$(3-pyridyl)]$_2$; $R^{40}$ is H or methyl; $R^{41}$ is methyl, ethyl 2-substituted with CO$_2$CH$_2$CH$_3$, morpholino or 1-imidazolidin-2-onyl; or $R^{40}$ and $R^{41}$ together with the nitrogen atom to which they are attached form a (4-CO$_2R^{43}$) piperidino or 4-($NR^{44}$)-1-piperazinyl group; $R^{43}$ is H or ethyl; and $R^{44}$ is H, methyl or 2-hydroxyethyl.

Preferred individual compounds of formula (VI) include:

2-[2-ethoxy-5-(4-ethoxycarbonylpiperidinosulfonyl)phenyl]-8-n-propylpyrido[3,2-d]pyrimidin-4(3H)-one;

2-[5-(4-carboxypiperidinosulfonyl)-2-ethoxyphenyl]-8-n-propylpyrido[3,2-d]pyrimidin-4(3H)-one;

2-{2-ethoxy-5-[4-(2-hydroxyethyl)-1-piperazinylsulfonyl]phenyl}-8-n-propyl pyrido[3,2-d]pyrimidin-4(3H)-one; and 2-{2-ethoxy-5-[(bis-3-pyridylsulfonyl)amino]phenyl}-8-n-propylpyrido[3,2-d]pyrimidin-4(3H)-one.

Preferred compounds of formula (VII) include those wherein $R^{45}$ is n-propyl; $R^{46}$ is H or methyl; $R^{47}$ is ethyl or n-propyl; $R^{48}$ is ethyl substituted with $CONR^{49}R^{50}$ or $CO_2R^{51}$, vinyl substituted with $CONR^{49}R^{50}$ or $CO_2R^{51}$, acetyl substituted with $NR^{49}R^{50}$, or $SO_2NR^{49}R^{50}$, or $CONR^{49}R^{50}$, or $CO_2R^{51}$, or bromo; $R^{49}$ and $R^{50}$ together with the nitrogen atom to which they are attached form a morpholino, 4-($NR^{52}$)-1-piperazinyl or 2,4-dimethyl-1-imidazolyl group; $R^{51}$ is H or t-butyl; and $R^{52}$ is methyl or 2-hydroxyethyl.

Preferred individual compounds of formula (VII) include:

6-(5-bromo-2-n-propoxyphenyl)-3-methyl-1-n-propyl-1,5-dihydro-4H-pyrazolo[3,4-d]pyrimidin-4-one;

3-methyl-6-(5-morpholinosulfonyl-2-n-propoxyphenyl)-1-n-propyl-1,5-dihydro-4H-pyrazolo[3,4-d]pyrimidin-4-one;

6-[5-(2-carboxyvinyl)-2-n-propoxyphenyl]-3-methyl-1-n-propyl-1,5-dihydro-4H-pyrazolo[3,4-d]pyrimidin-4-one;

6-[5-(2-t-butoxycarbonylvinyl)-2-n-propoxyphenyl]-3-methyl-1-n-propyl-1,5-dihydro-4H-pyrazolo[3,4-d]pyrimidin-4-one;

3-methyl-6-[5-(2-morpholinocarbonylvinyl)-2-n-propoxyphenyl]-1-n-propyl-1,5-dihydro-4H-pyrazolo[3,4-d]pyrimidin-4-one; and 3-methyl-6-[5-(2-morpholinocarbonylethyl)-2-n-propoxyphenyl]-1-n-propyl-1,5-dihydro-4H-pyrazolo[3,4-d]pyrimidin-4-one.

Preferred compounds of formula (VIII) include those wherein $R^{65}$ is H, methyl or ethyl; and $R^{56}$ is $C_1-C_6$ alkyl optionally substituted with cyclohexyl or with morpholino.

Preferred individual compounds of formula (VIII) include:

5-[2-ethoxy-5-(3-morpholinopropylsulfamoyl)-phenyl]-1,3-dimethyl-1,6-dihydro-7H-pyrazolo[4,3-d]pyrimidin-7-one;

1-ethyl-5-[5-(n-hexylsulfamoyl)-2-n-propoxyphenyl]-3-methyl-1,6-dihydro-7H-pyrazolo[4,3-d]pyrimidin-7-one;

1-ethyl-5-(5-diethylsulfamoyl-2-n-propoxyphenyl)-3-methyl-1,6-dihydro-7H-pyrazolo[4,3-d]pyrimidin-7-one; and 5-[5-(N-cyclohexylmethyl-N-methylsulfamoyl)-2-n-propoxyphenyl]1-ethyl-3-methyl-1,6-dihydro-7H-pyrazolo[4,3-d]pyrimidin-7-one.

Preferred compounds of formula (IX) include those wherein: $R^{57}$ is (a) hydrogen or halogen, e.g., fluorine; or (b) hydrogen.

Preferred compounds of formula (IX) also include those wherein: $R^{58}$ is (a) hydrogen, $C_{1-6}$ alkyl, halo $C_{1-6}$ alkyl, $C_{3-8}$ cycloalkyl, $C_{3-8}$ cycloalkyl $C_{1-3}$ alkyl, aryl $C_{1-3}$ alkyl or heteroaryl $C_{1-3}$ alkyl; (b) hydrogen, $C_{1-4}$ alkyl, halo $C_{1-4}$ alkyl, $C_{3-6}$ cycloalkyl, $C_{3-6}$ cycloalkylmethyl, pyridyl $C_{1-3}$ alkyl, furyl $C_{1-3}$ alkyl or optionally substituted benzyl, such as benzyl or halobenzyl, e.g., fluorobenzyl; or (c) $C_{1-4}$ alkyl, e.g., methyl, ethyl, isopropyl and n-butyl, $C_{3-6}$ cycloalkyl, e.g., cyclopentyl, or $C_{3-6}$ cycloalkylmethyl, e.g., cyclopropylmethyl.

Preferred compounds of formula (IX) further include those wherein: $R^{59}$ is (a) an optionally substituted benzene, thiophene, furan, pyridine or naphthalene ring or an optionally substituted bicyclic ring

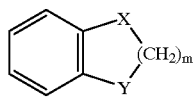

where m is 1 or 2 and X and Y are each $CH_2$ or O; (b) a substituted benzene ring such as benzene substituted by $C_{1-3}$ alkoxy, e.g., methoxy, or by $C_{1-3}$ alkoxy and by halogen, e.g., chlorine, or preferably, 4-methoxyphenyl or 3-chloro-4-methoxyphenyl; or (c) 3,4-methylenedioxyphenyl.

Preferred compounds of formula (IX) further yet include those wherein: $R^{60}$ is hydrogen, or $R^{58}$ and $R^{60}$ together are a 3-membered alkyl chain.

Preferred individual compounds of formula (IX) include:

cis-2,3,6,7,12,12a-hexahydro-2-(4-pyridylmethyl)-6-(3,4-methylenedioxyphenyl)-pyrazino[2',1':6,1]pyrido[3,4-b]indole-1,4-dione;

cis-2,3,6,7,12,12a-hexahydro-6-(2,3-dihydrobenzo[b]furan-5-yl)-2-methyl-pyrazino[2',1':6,1]pyrido[3,4-b]indole-1,4-dione;

cis-2,3,6,7,12,12a-hexahydro-6-(5-bromo-2-thienyl)-2-methyl-pyrazino[2',1':6,1]pyrido[3,4-b]indole-1,4-dione;

cis-2,3,6,7,12,12a-hexahydro-2-butyl-6-(4-methylphenyl)pyrazino[2',1':6,1]pyrido[3,4-b]indole-1,4-dione;

cis-2,3,6,7,12,12a-hexahydro-2-cyclopropyl-6-(3,4-methylenedioxy-phenyl)-pyrazino[2',1':6,1]pyrido[3,4-b]indole-1,4-dione;

(3S,6R,12aR)-2,3,6,7,12,12a-hexahydro-3-methyl-6-(3,4-methylenedioxyphenyl)-pyrazino[2',1':6,1]pyrido[3,4-b]indole-1,4-dione;

(3S,6R,12aR)-2,3,6,7,12,12a-hexahydro-2,3-dimethyl-6-(3,4-methylenedioxyphenyl)-pyrazino[2',1':6,1]pyrido[3,4-b]indole-1,4-dione;

(6R,12aR)-2,3,6,7,12,12a-hexahydro-2-isopropyl-6-(3,4-methylenedioxyphenyl)-pyrazino[2',1':6,1]pyrido[3,4-b]indole-1,4-dione;

(6R,12aR)-2,3,6,7,12,12a-hexahydro-2-cyclopentyl-6-(3,4-methylenedioxyphenyl)-pyrazino[2',1':6,1]pyrido[3,4-b]indole-1,4-dione;

(6R,12aR)-2,3,6,7,12,12a-hexahydro-2-cyclopropylmethyl-6-(4-methoxyphenyl)-pyrazino[2',1':6,1]pyrido[3,4-b]indole-1,4-dione;

(6R,12aR)-2,3,6,7,12,12a-hexahydro-6-(3-chloro-4-methoxyphenyl)-2-methyl-pyrazino[2',1':6,1]pyrido[3,4-b]indole-1,4-dione;

(6R,12aR)-2,3,6,7,12,12a-hexahydro-2-methyl-6-(3,4-methylenedioxyphenyl)-pyrazino[2',1':6,1]pyrido[3,4-b]indole-1,4-dione;

(6R,12aR)-2,3,6,7,12,12a-hexahydro-6-(3,4-methylenedioxyphenyl)-pyrazino[2',1':6,1]pyrido[3,4-b]indole-1,4-dione;

(5aR,12R,14aS)-1,2,3,5,6,11,12,14a-octahydro-12-(3,4-methylenedioxyphenyl)-pyrrolo[1",2":4',5']pyrazino[2',1':6,1]pyrido[3,4-b]indole-5-1,4-dione; and pharmaceutically acceptable salts thereof.

Particularly preferred individual compounds of formula (IX) are (6R,12aR)-2,3,6,7,12,12a-hexahydro-2-methyl-6-(3,4-methylenedioxyphenyl)-pyrazino[2',1':6,1]pyrido[3,4-b]indole-1,4-dione and (3S,6R,12aR)-2,3,6,7,12,12a-hexahydro-2,3-dimethyl-6-(3,4-methylenedioxyphenyl)-pyrazino[2',1':6,1]pyrido[3,4-b]indole-1,4-dione, and the pharmaceutically acceptable salts thereof.

Preferred compounds of formulae (XA) and (XB) include those wherein: $R^{61}$ is $C_1-C_2$ alkyl substituted with $C_3-C_5$ cycloalkyl, $CONR^{65}R^{66}$ or a N-linked heterocyclic group selected from pyrazolyl, triazolyl, morpholinyl and 4-$R^{67}$-piperazinyl; $(CH_2)_p$Het or $(CH_2)_q$Ar; $R^{65}$ is H; $R^{66}$ is $C_1-C_4$ alkyl optionally substituted with $C_1-C_4$ alkoxy, or, $R^{65}$ and $R^{66}$ together with the nitrogen atom to which they are attached, form a morpholinyl group; Het is selected from pyridinyl, 1-oxidopyridinyl, pyridazinyl, pyrimidinyl, pyrazinyl, imidazolyl, isoxazolyl, thiazolyl, triazolyl and oxadiazolyl, any of which is optionally substituted with one or two substituents selected from $C_3$, $CH_2CH_2OCH_3$, $OCH_3$ and $NH_2$.

Other preferred compounds of formulae (XA) and (XB) include those wherein: $R^{61}$ is $C_1-C_2$ alkyl substituted with cyclobutyl, CONR$^{65}$R$^{66}$, pyrazol-1-yl, 1,2,3-triazol-1-yl, 1,2,4-triazol-1-yl, morpholin-4-yl or 4-methylpiperazin-1-yl; pyrimidin-2-yl; CH$_2$Het or (CH$_2$)$_q$Ar; R$^{62}$ is C$_1$–C$_3$ alkyl; R$^{63}$ is C$_1$–C$_3$ alkyl optionally substituted with C$_1$–C$_2$ alkoxy; R$^{65}$ is H; R$^{66}$ is C$_1$–C$_2$ alkyl optionally substituted with C$_1$–C$_2$ alkoxy, or, R$^{65}$ and R$^{66}$ together with the nitrogen atom to which they are attached, form a morpholin-4-yl group; R$^{70}$ is C$_1$–C$_2$ alkyl optionally monosubstituted with OH, OCH$_3$ or CONH$_2$; Het is selected from pyridin-2-yl, 1-oxidopyridin-2-yl, pyridin-3-yl, pyridazin-3-yl, pyridazin-4-yl, pyrimidin-4-yl, pyrimidin-5-yl, pyrazin-2-yl, 3-methoxypyridin-2-yl, 6-aminopyridin-2-yl, 1-methylimidazol-2-yl, 3,5-dimethylisoxazol-4-yl, 2-methylthiazol-4-yl, 1-methyl-1,2,4-triazol-5-yl, 1-(2-methoxyethyl)-1,2,4-triazol-5-yl, 4-methyl-1,2,4-triazol-3-yl, 3-methyl-1,2,4-triazol-5-yl, 1,2,4-oxadiazol-3-yl and 5-methyl-1,2,4-oxadiazol-3-yl; Ar is selected from phenyl, 4-chlorophenyl, 4-bromophenyl, 2-cyanophenyl, 2-carbamoylphenyl, 4-carbamoylphenyl, 2-nitrophenyl, 4-nitrophenyl, 2-aminophenyl, 4-aminophenyl, 2-methanesulfonamidophenyl, 4-methanesulfonamidophenyl, 4-ethanesulfonamidophenyl, 4-(prop-2-ylsulfonamido)phenyl and 4-sulfamoylphenyl.

Further preferred compounds of formulae (XA) and (XB) include those wherein: R$^{61}$ is cyclobutylmethyl, morpholin-4-ylcarbonylmethyl, 2-(morpholin-4-yl)ethyl, pyrimidin-2-yl, CH$_2$Het or (CH$_2$)$_q$Ar; R$^{62}$ is CH$_2$CH$_3$ or CH$_2$CH$_2$CH$_3$; R$^{63}$ is CH$_2$CH$_3$, CH$_2$CH$_2$CH$_3$ or CH$_2$CH$_2$OCH$_3$; R$^{70}$ is CH$_3$, CH$_2$CH$_3$ or CH$_2$CH$_2$OH; Het is selected from pyridin-2-yl, pyridazin-3-yl, pyrazin-2-yl, 3-methoxypyridin-2-yl, 6-aminopyridin-2-yl, 1-methylimidazol-2-yl, 3,5-dimethylisoxazol-4-yl, 1-methyl-1,2,4-triazol-5-yl, 1-(2-methoxyethyl)-1,2,4-triazol-5-yl and 5-methyl-1,2,4-oxadiazol-3-yl; Ar is selected from phenyl, 2-aminophenyl, 2-methanesulfonamidophenyl, 4-methanesulfonamidophenyl, 4-ethanesulfonamidophenyl and 4-(prop-2-ylsulfonamido)phenyl.

Preferred individual compounds of formulae (XA) and (XB) include:

- 5-{5-[4-(2-hydroxyethyl)piperazin-1-ylsulfonyl]-2-n-propoxyphenyl}-3-n-propyl-1-(pyridin-2-yl)methyl-1,6-dihydro-7H-pyrazolo[4,3-d]pyrimidin-7-one;
- 1-(1-methylimidazol-2-yl)methyl-5-[5-(4-methylpiperazin-1-ylsulfonyl)-2-n-propoxyphenyl]-3-n-propyl-1,6-dihydro-7H-pyrazolo[4,3-d]pyrimidin-7-one;
- 5-{5-[4-(2-hydroxyethyl)piperazin-1-ylsulfonyl]-2-n-propoxyphenyl}-3-n-propyl-2-(pyridin-2-yl)methyl-2,6-dihydro-7H-pyrazolo[4,3-d]pyrimidin-7-one;
- 5-[5-(4-ethylpiperazin-1-ylsulfonyl)-2-n-propoxyphenyl]-3-n-propyl-2-(pyridin-2-yl)methyl-2,6-dihydro-7H-pyrazolo[4,3-d]pyrimidin-7-one;
- 3-ethyl-5-[5-(4-ethylpiperazin-1-ylsulfonyl)-2-n-propoxyphenyl]-2-(pyridin-2-yl)methyl-2,6-dihydro-7H-pyrazolo[4,3-d]pyrimidin-7-one;
- 5-[5-(4-ethylpiperazin-1-ylsulfonyl)-2-n-propoxyphenyl]-3-n-propyl-2-(pyridazin-3-yl)methyl-2,6-dihydro-7H-pyrazolo[4,3-d]pyrimidin-7-one;
- 5-[5-(4-ethylpiperazin-1-ylsulfonyl)-2-n-propoxyphenyl]-3-n-propyl-2-(pyridazin-2-yl)methyl-2,6-dihydro-7H-pyrazolo[4,3-d]pyrimidin-7-one; and
- 5-[2-ethoxy-5-(4-ethylpiperazin-1-ylsulfonyl)phenyl]-3-n-propyl-2-(pyridin-2-yl)methyl-2,6-dihydro-7H-pyrazolo[4,3-d]pyrimidin-7-one.

As discussed above, the compounds of the present invention possess cGMP PDE inhibitory activity and are described herein as useful in treating, e.g., preventing, reducing and/or reversing, nitrate-induced tolerance. Test methods for determining the cGMP PDE inhibitory activities of the compounds, or the pharmaceutically acceptable salts, prodrugs, polymorphs, hydrates, solvates, active metabolites or stereoisomers thereof, of the present invention can be understood and carried out by one skilled in the art in any suitable manner, e.g., according to one or more of the assays described in the aforementioned U.S. Pat. Nos. 5,250,534; 5,272,147; 5,294,612; 5,346,901; 5,488,055; 5,541,187; 5,614,530; 5,656,629; 5,482,941; 5,734,053; 5,736,548 and 5,591,742, and the International PCT Applications published as WO 93/06104; WO 93/07149; WO 93/12095; WO 94/00453; WO 94/05661; WO 94/28902; WO 95/19978; WO 96/16657; WO 96/28446; WO 96/28159; WO 96/28429; WO 96/28448; WO 97/03675 and WO 98/49166.

Test methods for determining the reduction and/or reversal of nitrate-induced tolerance of the compounds of formulae (I)–(XB) herein, or the pharmaceutically acceptable salts, prodrugs, polymorphs, hydrates, solvates, active metabolites or stereoisomers thereof, can be understood and carried out by one skilled in the art in any suitable manner, e.g., according to one or more of the assays described in the aforementioned U.S. Pat. Nos. 5,294,612; 5,488,055; 5,541,187; 5,614,530; 5,656,629 and 5,736,548, and International PCT Applications published as WO 96/28446; WO 96/28159; WO 96/28429; and WO 96/28448.

For administration to humans in the treatment, e.g., prophylactic, palliative, curative, prevention, reduction and/or reversal, of nitrate-induced tolerance, oral dosages of, e.g., a compound of formulae (I)–(XB), or any combination of the compounds of formulae (I)–(XB), or the pharmaceutically acceptable salts, prodrugs, polymorphs, hydrates, solvates, active metabolites or stereoisomers thereof (the active compounds), are generally in the range of from about 0.1 mg to about 1000 mg per day for an average adult patient (about 70 kg). Individual tablets or capsules should generally contain from about 0.1 mg to about 1000 mg of active compound, in a suitable pharmaceutically acceptable vehicle, diluent or carrier. Dosages for intravenous administration are typically within the range of from about 0.1 mg to about 500 mg per single dose as required. For intranasal or inhaler administration, the dosage is generally formulated as from about a 0.1% to about a 1% (w/v) solution. In practice, the physician will determine the actual dosage which will be most suitable for an individual patient and it will vary with age, weight and response of the particular patient. The above dosages are exemplary of the average case but there can, of course, be individual instances where higher or lower dosage ranges are merited, and all such dosages are within the scope of the present invention.

In addition, the treating physician will understand from the present disclosure how to select any suitable dosage of any suitable organic nitrate ester. For example, the treating physician will understand for any individual instance whether to lower the dosage of organic nitrate ester exemplary of the average case depending upon any suitable factors, e.g., when administering a particularly efficacious compound of the present invention where efficacious means the ability of the compound of the present invention to treat nitrate-induced tolerance.

For human use, the active compounds of the present invention can be administered alone, but will generally be administered in an admixture with a pharmaceutically acceptable vehicle, diluent or carrier selected with regard to the intended route of administration and standard pharmaceutical practice. For example, they may be administered orally in the form of tablets comprising such excipients as starch or lactose, or in capsules either alone or in admixture with excipients, or in the form of elixirs or suspensions comprising flavoring or coloring agents. They may be injected parenterally; for example, intravenously, intramuscularly or subcutaneously. For parenteral administration, they are best used in the form of a sterile aqueous solution which may contain other substances; for example, enough salts or glucose to make the solution isotonic.

Additionally, the active compounds may be administered topically and this may be done by way of creams, jellies, gels, pastes, and ointments, in accordance with standard pharmaceutical practice.

The active compounds may also be administered to a mammal other than a human such as, for example, a companion animal. The dosage to be administered will depend, for example, on the species and the disease or disorder being treated. The active compounds may be administered in the form of a capsule, bolus, tablet or liquid drench. The active compounds may also be administered by injection or as an implant. Such formulations are prepared in a conventional manner in accordance with standard veterinary practice. As an alternative, the compounds of the present invention may be administered with the feedstuff and for this purpose a concentrated feed additive or premix may be prepared for mixing with the normal feed.

The ability of the compounds, or the pharmaceutically acceptable salts, prodrugs, polymorphs, hydrates, solvates, active metabolites or stereoisomers thereof, of the novel methods and pharmaceutical compositions of the present invention, to inhibit cGMP PDE may be determined using a suitable method such as, for example, the assay described immediately below.

Compound affinities for cGMP and cAMP PDEs are assessed by determination of their $IC_{50}$ values (the concentration of inhibitor required for 50% inhibition of enzyme activity). The PDE enzymes are isolated from rabbit platelets and rat kidney, essentially by the method of W. J. Thompson and M. M. Appleman, *Biochem.* 10: 311 (1971). The calcium/calmodulin (Ca/CAM)-independent cGMP PDE and the cGMP-inhibited cAMP PDE enzymes are obtained from rabbit platelets while, of the four major PDE enzymes of the rat kidney, the Ca/CAM-dependent cGMP PDE (fraction I) is isolated. Assays are performed using a modification of the "batch" method of W. J. Thompson et al., *Biochem.* 18:5228 (1979).

The ability of the compounds, or the pharmaceutically acceptable salts, prodrugs, polymorphs, hydrates, solvates, active metabolites or stereoisomers thereof, of the novel methods and pharmaceutical compositions of the present invention, to reduce and/or reverse nitrate-induced tolerance may be determined using a suitable method such as, for example, the assay described immediately below.

Spontaneously hypertensive rats (from about 17 to about 25 weeks of age) are made nitroglycerin tolerant by repeated (three times per day for three consecutive days) administration (subcutaneously) of high doses of nitroglycerin (about 100 mg/kg). To confirm tolerance, challenge doses of nitroglycerin are administered (intravenously) at doses ranging from about 1 μg/kg to about 300 μg/kg and the maximum change in mean arterial pressure (MAP) for each dose is recorded.

Groups of tolerant rats are pretreated (intravenously) with representative compounds of the invention (tolerant pretreated group) or with vehicle (0.05N NaOH) (tolerant vehicle pretreated group) 5–10 minutes prior to the administration of challenge doses of nitroglycerin. A dose-MAP curve is generated, and the area under the dose-MAP curve is calculated for the non-tolerant group and for the tolerant vehicle pretreated group and the tolerant pretreated group. The percent reversal of nitrate-induced tolerance is calculated as follows:

$$\text{Percent reversal} = \frac{(AUC_{tol-pretreated} - AUC_{tol-veh})}{(AUC_{nontol} - AUC_{tol-veh})} \times 100$$

wherein: $AUC_{tol-pretreated}$ is the area under the dose-MAP curve for the tolerant pretreated group; $AUC_{tol-veh}$ is the area under the dose-MAP curve for the tolerant vehicle pretreated group; and $AUC_{nontol}$ is the area under the dose-MAP curve for the non-tolerant group. A percent reversal of 100% or greater indicates that a complete reversal of nitrate-induced tolerance has occurred, while a percent reversal of 0% indicates that no reversal of nitrate-induced tolerance has occurred.

What is claimed is:

1. A method of treating nitrate-induced tolerance in a mammal comprising administering to said mammal a nitrate-induced tolerance treating amount of a compound of formula (I)

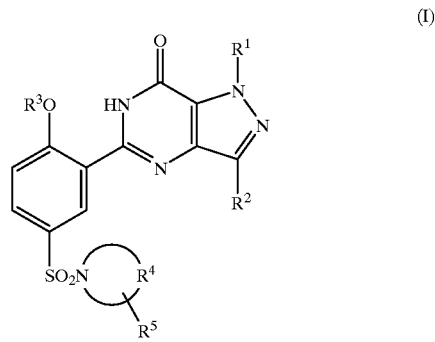

(I)

and the pharmaceutically acceptable salts, prodrugs, polymorphs, hydrates, solvates, active metabolites and stereoisomers thereof; wherein:

$R^1$ is H, $C_1-C_3$ alkyl, $C_3-C_5$ cycloalkyl or $C_1-C_3$ perfluoroalkyl;

$R^2$ is H, $C_1-C_6$ alkyl optionally substituted by OH, $C_1-C_3$ alkoxy or $C_3-C_6$ cycloalkyl, or $C_1-C_3$ perfluoroalkyl;

$R^3$ is $C_1-C_6$ alkyl, $C_3-C_6$ alkenyl, $C_3-C_6$ alkynyl, $C_3-C_7$ cycloalkyl, $C_1-C_6$ perfluoroalkyl or $(C_3-C_6$ cycloalkyl)$C_1-C_6$ alkyl;

$R^4$ taken together with the nitrogen atom to which it is attached completes a 4-N—($R^6$)-piperazinyl group;

$R^5$ is H, $C_1-C_4$ alkyl, $C_1-C_3$ alkoxy, $NR^7R^8$ or $CONR^7R^8$;

$R^6$ is H, $C_1-C_6$ alkyl, $(C_1-C_3$ alkoxy)$C_2-C_6$ alkyl, hydroxy $C_2-C_6$ alkyl, $(R^7R^8N)C_2-C_6$ alkyl, $(R^7R^8NCO)C_1-C_6$ alkyl, $CONR^7R^8$, $CSNR^7R^8$ or $C(NH)NR^7R^8$; and $R^7$ and $R^8$ are each independently H, $C_1-C_4$ alkyl, $(C_1-C_3$ alkoxy)$C_2-C_4$ alkyl or hydroxy $C_2-C_4$ alkyl;

a compound of formula (II)

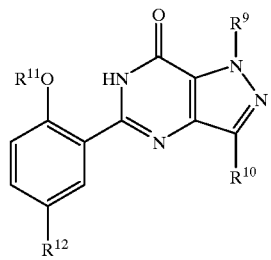

(II)

and the pharmaceutically acceptable salts, prodrugs, polymorphs, hydrates, solvates, active metabolites and stereoisomers thereof; wherein:

$R^9$ is H, $C_1$–$C_3$ alkyl optionally substituted with one or more fluoro substituents, or $C_3$–$C_5$ cycloalkyl;

$R^{10}$ is H or $C_1$–$C_6$ alkyl optionally substituted with one or more fluoro substituents or with $C_3$–$C_6$ cycloalkyl;

$R^{11}$ is $C_1$–$C_6$ alkyl optionally substituted with one or more fluoro substituents or with $C_3$–$C_6$ cycloalkyl, or $C_3$–$C_5$ cycloalkyl, or $C_3$–$C_6$ alkenyl, or $C_3$–$C_6$ alkynyl;

$R^{12}$ is $C_1$–$C_4$ alkyl optionally substituted with OH, $NR^{13}R^{14}$, CN, $CONR^{13}R^{14}$ or with $CO_2R^{15}$, or $C_2$–$C_4$ alkenyl optionally substituted with CN, $CONR^{13}R^{14}$ or with $CO_2R^{15}$, or $C_2$–$C_4$ alkanoyl optionally substituted with $NR^{13}R^{14}$, or hydroxy $C_2$–$C_4$ alky optionally substituted with $NR^{13}R^{14}$, or ($C_2$–$C_3$ alkoxy)$C_1$–$C_2$ alkyl optionally substituted with OH or $NR^{13}R^{14}$, or $CONR^{13}R^{14}$, or $CO_2R^{15}$, or halo, or $NR^{13}R^{14}$, or $NHSO_2NR^{13}R^{14}$, or $NHSO_2R^{16}$, or phenyl or heterocyclyl either of which is optionally substituted with methyl;

$R^{13}$ and $R^{14}$ are each independently H, $C_1$–$C_4$ alkyl, or together with the nitrogen atom to which they are attached form a pyrrolidinyl, piperidino, morpholino, 4-($NR^{17}$)-piperazinyl or imidazolyl group wherein said group is optionally substituted with methyl or hydroxy;

$R^{15}$ is H or $C_1$–$C_4$ alkyl;

$R^{16}$ is $C_1$–$C_3$ alkyl optionally substituted with $NR^{13}R^{14}$; and $R^{17}$ is H, $C_1$–$C_3$ alkyl optionally substituted with phenyl, or hydroxy $C_2$–$C_3$ alkyl, or $C_1$–$C_4$ alkanoyl;

a compound of formula (III)

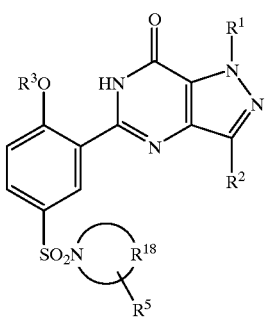

(III)

and the pharmaceutically acceptable salts, prodrugs, polymorphs, hydrates, solvates, active metabolites and stereoisomers thereof; wherein: $R^1$, $R^2$, $R^3$ and $R^5$ are as previously described for said formula (I); $R^{18}$ taken together with the nitrogen to which it is attached completes a pyrrolidinyl, piperidino or morpholino group;

a compound of formula (IV)

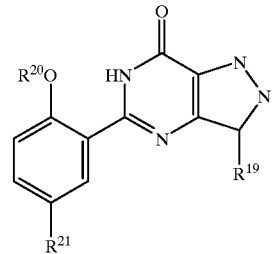

(IV)

and the pharmaceutically acceptable salts, prodrugs, polymorphs, hydrates, solvates, active metabolites and stereoisomers thereof; wherein:

$R^{19}$ is $C_1$–$C_4$ alkyl;

$R^{20}$ is $C_2$–$C_4$ alkyl;

$R^{21}$ is H or $SO_2NR^{22}R^{23}$;

$R^{22}$ and $R^{23}$ together with the nitrogen atom to which they are attached form a pyrrolidino, piperidino, morpholino or 4-N—($R^{24}$)-1-piperazinyl group; and $R^{24}$ is H or $C_1$–$C_3$ alkyl;

a compound of formula (V)

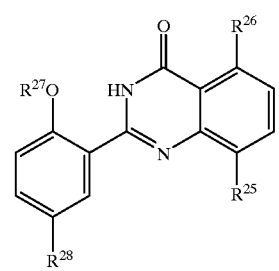

(V)

and the pharmaceutically acceptable salts, prodrugs, polymorphs, hydrates, solvates, active metabolites and stereoisomers thereof; wherein:

$R^{25}$ is H, $C_1$–$C_4$ alkyl, $C_1$–$C_4$ alkoxy or $CONR^{29}R^{30}$;

$R^{26}$ is H or $C_1$–$C_4$ alkyl;

$R^{27}$ is $C_2$–$C_4$ alkyl;

$R^{28}$ is H, $C_2$–$C_4$ alkanoyl optionally substituted with $NR^{31}R^{32}$, or (hydroxy)$C_2$–$C_4$ alkyl optionally substituted with $NR^{31}R^{32}$, or $CH=CHCO_2R^{33}$, or $CH=CHCONR^{31}R^{32}$, or $CH_2CH_2CO_2R^{33}$, or $CH_2CH_2CONR^{31}R^{32}$, or $SO_2NR^{31}R^{32}$, or $SO_2NH(CH_2)_nNR^{31}R^{32}$ or imidazolyl;

$R^{29}$ and $R^{30}$ are each independently H or $C_1$–$C_4$ alkyl;

$R^{31}$ and $R^{32}$ are each independently H or $C_1$–$C_4$ alkyl, or together with the nitrogen atom to which they are attached form a pyrrolidino, piperidino, morpholino or 4-($NR^{34}$)-1-piperazinyl group wherein any of said groups is optionally substituted with $CONR^{29}R^{30}$;

$R^{33}$ is H or $C_1$–$C_4$ alkyl;

$R^{34}$ is H, $C_1$–$C_3$ alkyl or (hydroxy)$C_2$–$C_3$ alkyl; and n is 2, 3 or 4; and provided that $R^{28}$ is not H when $R^{25}$ is H, $C_1$–$C_4$ alkyl or $C_1$–$C_4$ alkoxy;

a compound of formula (VI)

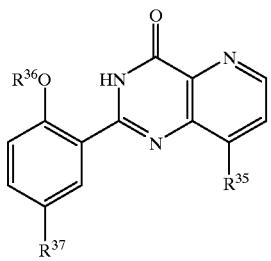

and the pharmaceutically acceptable salts, prodrugs, polymorphs, hydrates, solvates, active metabolites and stereoisomers thereof; wherein:

$R^{35}$ is H, $C_1$–$C_4$ alkyl, CN or $CONR^{29}R^{30}$;

$R^{36}$ is $C_2$–$C_4$ alkyl;

$R^{37}$ is $SO_2NR^{38}R^{39}$, $NO_2$, $NH_2$, $NHCOR^{42}$, $NHSO_2R^{42}$ or $N(SO_2R^{42})_2$;

$R^{38}$ and $R^{39}$ are each independently selected from H and $C_1$–$C_4$ alkyl optionally substituted with $CO_2R^{43}$, OH, pyridyl, 5-isoxazolin-3-onyl, morpholino or 1-imidazolidin-2-onyl, or together with the nitrogen atom to which they are attached form a pyrrolidino, piperidino, morpholino, 1-pyrazolyl or 4-($NR^{44}$)-1-piperazinyl group wherein any of said groups may optionally be substituted with one or two substituents selected from $C_1$–$C_4$ alkyl, $CO_2R^{43}$, $NH_2$ and OH;

$R^{42}$ is $C_1$–$C_4$ alkyl or pyridyl;

$R^{43}$ is H or $C_1$–$C_4$ alkyl; and $R^{44}$ is H, $C_1$–$C_4$ alkyl or (hydroxy)$C_2$–$C_3$ alkyl;

a compound of formula (VII)

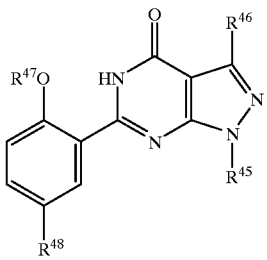

and the pharmaceutically acceptable salts, prodrugs, polymorphs, hydrates, solvates, active metabolites and stereoisomers thereof; wherein:

$R^{45}$ is $C_1$–$C_6$ alkyl;

$R^{46}$ is H, methyl or ethyl;

$R^{47}$ is $C_2$–$C_4$ alkyl;

$R^{48}$ is $C_1$–$C_4$ alkyl optionally substituted with $NR^{49}R^{50}$, CN, $CONR^{49}R^{50}$ or $CO_2R^{51}$; $C_2$–$C_4$ alkenyl optionally substituted with CN, $CONR^{49}R^{50}$ or $CO_2R^{51}$; $C_2$–$C_4$ alkanoyl optionally substituted with $NR^{49}R^{50}$; $SO_2NR^{49}R^{50}$; $CONR^{49}R^{50}$; $CO_2R^{51}$; or halo;

$R^{49}$ and $R^{50}$ are each independently H or $C_1$–$C_4$ alkyl, or together with the nitrogen atom to which they are attached form a pyrrolidino, piperidino, morpholino, 4-($NR^{52}$)-1-piperazinyl or 1-imidazolyl group wherein said group is optionally substituted by one or two $C_1$–$C_4$ alkyl groups;

$R^{51}$ is H or $C_1$–$C_4$ alkyl; and $R^{52}$ is H, $C_1$–$C_3$ alkyl or hydroxy $C_2$–$C_3$ alkyl;

a compound of formula (VIII)

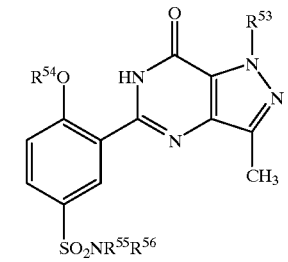

and the pharmaceutically acceptable salts, prodrugs, polymorphs, hydrates, solvates, active metabolites and stereoisomers thereof; wherein:

$R^{53}$ is methyl or ethyl;

$R^{54}$ is ethyl or n-propyl;

$R^{55}$ and $R^{56}$ are each independently H or $C_1$–$C_6$ alkyl optionally substituted with $C_5$–$C_7$ cycloalkyl or with morpholino; or a compound of formula (IX)

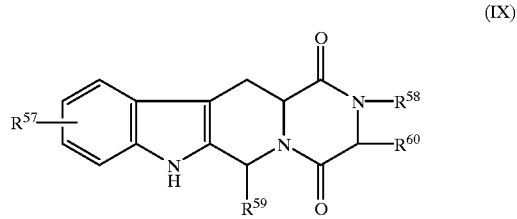

and the pharmaceutically acceptable salts, prodrugs, polymorphs, hydrates, solvates, active metabolites and stereoisomers thereof; wherein:

$R^{57}$ is hydrogen, halogen or $C_{1-6}$ alkyl;

$R^{58}$ is hydrogen, $C_{1-6}$ alkyl, $C_{2-6}$ alkenyl, $C_{2-6}$ alkynyl, halo $C_{1-6}$ alkyl, $C_{3-8}$ cycloalkyl, $C_{3-8}$ cycloalkyl $C_{1-3}$ alkyl, aryl $C_{1-3}$ alkyl or heteroaryl $C_{1-3}$ alkyl;

$R^{59}$ is an optionally substituted monocyclic aromatic ring selected from benzene, thiophene, furan and pyridine or an optionally substituted bicyclic ring

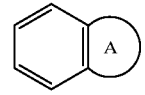

attached to the rest of the molecule via one of the benzene ring carbon atoms and wherein the fused ring A is a 5- or 6-membered ring which may be saturated or partially or fully unsaturated and comprises carbon atoms and optionally one or two heteroatoms selected from oxygen, sulphur and nitrogen; and $R^{60}$ is hydrogen or $C_{1-3}$ alkyl, or $R^{58}$ and $R^{60}$ together represent a 3- or 4-membered alkyl or alkenyl chain; or a compound of formulae (XA) or (XB)

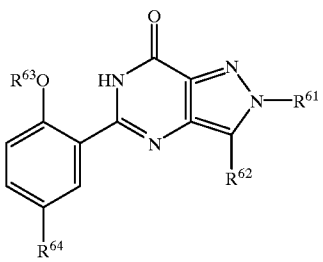
(XA)

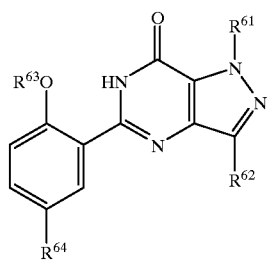
(XB)

and the pharmaceutically acceptable salts, prodrugs, polymorphs, hydrates, solvates, active metabolites and stereoisomers thereof; wherein:

$R^{61}$ is $C_1$–$C_3$ alkyl substituted with $C_3$–$C_6$ cycloalkyl, $CONR^{65}R^{66}$ or a N-linked heterocyclic group selected from pyrazolyl, imidazolyl, triazolyl, pyrrolidinyl, piperidinyl, morpholinyl and 4-$R^{67}$-piperazinyl; $(CH_2)_p$Het or $(CH_2)_q$Ar;

$R^{62}$ is $C_1$–$C_6$ alkyl;

$R^{63}$ is $C_1$–$C_6$ alkyl optionally substituted with $C_1$–$C_4$ alkoxy;

$R^{64}$ is $SO_2NR^{68}R^{69}$;

$R^{65}$ and $R^{66}$ are each independently selected from H and $C_1$–$C_4$ alkyl optionally substituted with $C_1$–$C_4$ alkoxy, or, together with the nitrogen atom to which they are attached, form a pyrrolidinyl, piperidinyl, morpholinyl or 4-$R^{67}$-piperazinyl group;

$R^{68}$ and $R^{69}$, together with the nitrogen atom to which they are attached, form a 4-$R^{70}$-piperazinyl group;

$R^{67}$ is $C_1$–$C_4$ alkyl;

$R^{70}$ is H or $C_1$–$C_4$ alkyl optionally substituted with OH, $C_1$–$C_4$ alkoxy or $CONH_2$;

Het is a C-linked 6-membered heterocyclic group containing one or two nitrogen atoms, optionally in the form of of its mono-N-oxide, or a C-linked 5-membered heterocyclic group containing from one to four heteroatoms selected from nitrogen, oxygen and sulfur, wherein either of said heterocyclic groups is optionally substituted with one or two substituents selected from $C_1$–$C_4$ alkyl optionally substituted with $C_1$–$C_4$ alkoxy, $C_1$–$C_4$ alkoxy, halo and $NH_2$;

Ar is phenyl optionally substituted with one or two substituents selected from $C_1$–$C_4$ alkyl, $C_1$–$C_4$ alkoxy, halo, CN, $CONH_2$, $NO_2$, $NH_2$, $NHSO_2$ ($C_1$–$C_4$ alkyl) and $SO_2NH_2$; and p and q are each independently 0 or 1.

2. A method as defined in claim 1 wherein in said formula (I) $R^1$ is H, methyl or ethyl; $R^2$ is $C_1$–$C_3$ alkyl optionally substituted by OH or methoxy; $R^3$ is $C_2$–$C_3$ alkyl or allyl; $R^4$ taken together with the nitrogen atom to which it is attached completes a piperidino or 4-N—($R^6$)-piperazinyl group; $R^5$ is H, $NR^7R^8$ or $CONR^7R^8$; $R^6$ is H, $C_1$–$C_3$ alkyl, hydroxy $C_2$–$C_3$ alkyl, $CONR^7R^8$, $CSNR^7R^8$ or $C(NH)NR^7R^8$; and $R^7$ and $R^8$ are each independently H or methyl.

3. A method as defined in claim 2 wherein $R^1$ is methyl; $R^2$ is n-propyl; $R^3$ is ethyl, n-propyl or allyl; $R^4$ taken together with the nitrogen atom to which it is attached forms a 4-N—($R^6$)-piperazinyl group; $R^5$ is H; and $R^6$ is H, $C_1$–$C_3$ alkyl or 2-hydroxyethyl.

4. A method as defined in claim 2 wherein $R^1$ is methyl; $R^2$ is n-propyl; $R^3$ is ethyl; $R^5$ is H; and $R^6$ is methyl.

5. A method as defined in claim 1 wherein in said formula (II) $R^9$ is H, methyl or ethyl; $R^{10}$ is $C_1$–$C_3$ alkyl; $R^{11}$ is $C_2$–$C_3$ alkyl; $R^{12}$ is $C_1$–$C_2$ alkyl optionally substituted with OH, $NR^{13}R^{14}$, $CONR^{13}R^{14}$ or with $CO_2R^{15}$, acetyl optionally substituted with $NR^{13}R^{14}$, or hydroxy ethyl substituted with $NR^{13}R^{14}$, or ethoxymethyl optionally substituted with OH or with $NR^{13}R^{14}$, or CH=CHCN, or CH=CHCONR$^{13}$R$^{14}$, or CH=CHCO$_2$R$^{15}$, or CO$_2$H, or Br, or $NR^{13}R^{14}$, or $CONR^{13}R^{14}$, or $NHSO_2NR^{13}R^{14}$, or $NHSO_2R^{16}$, or pyridinyl or imidazolyl either of which is optionally substituted with methyl; $R^{13}$ and $R^{14}$ are each independently H, methyl or ethyl, or together with the nitrogen atom to which they are attached form a piperidino, morpholino, 4-($NR^{17}$)-1-piperazinyl or imidazolyl group wherein said group is optionally substituted with methyl or hydroxy; $R^{15}$ is H or t-butyl; $R^{16}$ is methyl or $CH_2CH_2CH_2NR^{13}R^{14}$; and $R^{17}$ is H, methyl, benzyl, 2-hydroxyethyl or acetyl.

6. A method as defined in claim 5 wherein $R^9$ is methyl; $R^{10}$ is n-propyl; $R^{11}$ is ethyl or n-propyl; $R^{12}$ is $CH_2NR^{13}R^{14}$, $CH_2OCH_2CH_2NR^{13}R^{14}$, $CH_2OCH_2CH_3$, $CH_2OCH_2CH_2OH$, $COCH_2NR^{13}R^{14}$, $CH(OH)CH_2NR^{13}R^{14}$, $CH=CHCON(CH_3)_2$, $CH=CHCO_2R^{15}$, $CO_2H$, $CONR^{13}R^{14}$, $NHSO_2NR^{13}R^{14}$, $NHSO_2CH_2CH_2CH_2NR^{13}R^{14}$, 2-pyridyl, 1-imidazolyl or 1-methyl-2-imidazolyl; and $R^{13}$ and $R^{14}$ together with the nitrogen atom to which they are attached form a piperidino, 4-hydroxypiperidino, morpholino, 4-($NR^{17}$)-1-piperazinyl or 2-methyl-1-imidazolyl group.

7. A method as defined in claim 1 wherein in said formula (III) $R^1$ is H, methyl or ethyl; $R^2$ is $C_1$–$C_3$ alkyl optionally substituted by OH or methoxy; $R^3$ is $C_2$–$C_3$ alkyl or allyl; $R^{18}$ taken together with the nitrogen atom to which it is attached completes a piperidino group; $R^5$ is H, $NR^7R^8$ or $CONR^7R^8$; and $R^7$ and $R^8$ are each independently H or methyl.

8. A method as defined in claim 1 wherein in said formula (IV) $R^{19}$ and $R^{20}$ are each independently ethyl or n-propyl; and $R^{22}$ and $R^{23}$ together with the nitrogen atom to which they are attached form a 4-N—($R^{24}$)-1-piperazinyl group.

9. A method as defined in claim 8 wherein $R^{19}$ is n-propyl; $R^{20}$ is ethyl; and $R^{21}$ is 1-piperazinylsulphonyl or 4-methyl-1-piperazinylsulfonyl.

10. A method as defined in claim 1 wherein in said formula (V) $R^{25}$ is H, methoxy or $CONR^{29}R^{30}$; $R^{26}$ is H or methyl; $R^{27}$ is ethyl or n-propyl; $R^{28}$ is H, acetyl optionally substituted with $NR^{31}R^{32}$, or hydroxyethyl substituted with $NR^{31}R^{32}$, or CH=CHCO$_2$R$^{33}$, or CH=CHCONR$^{31}$R$^{32}$, or $CH_2CH_2CO_2R^{33}$, or $SO_2NR^{31}R^{32}$, or $SO_2NH(CH_2)_3NR^{31}R^{32}$ or 1-imidazolyl; $R^{29}$ and $R^{30}$ are each independently H or ethyl; $R^{31}$ and $R^{32}$ together with the nitrogen atom to which they are attached form a piperidino, 4-carbamoylpiperidino, morpholino or 4-($NR^{34}$)-1-piperazinyl group; $R^{33}$ is H or t-butyl; and $R^{34}$ is H, methyl or 2-hydroxyethyl; provided that $R^{28}$ is not H when $R^{25}$ is H or methoxy.

11. A method as defined in claim 10 wherein $R^{25}$ is methyl, $CONH_2$ or $CONHCH_2CH_3$; $R^{26}$ is H; $R^{28}$ is H, acetyl, 1-hydroxy-2-($NR^{31}R^{32}$)ethyl, $CH{=}CHCO_2C(CH_3)_3$, or $CH{=}CHCONR^{31}R^{32}$, or $SO_2NR^{31}R^{32}$ or 1-midazolyl; $R^{31}$ and $R^{32}$ together with the nitrogen atom to which they are attached form a 4-($NR^{34}$)-1-piperazinyl group; and $R^{34}$ is methyl or 2-hydroxyethyl; provided that $R^{28}$ is not H when $R^{25}$ is methyl.

12. A method as defined in claim 1 wherein in said formula (VI) $R^{35}$ is H, n-propyl, CN or $CONH_2$; $R^{36}$ is ethyl; $R^{37}$ is $SO_2NR^{40}R^{41}$, $NO_2$, $NH_2$, $NHCOCH(CH_3)_2$, $NHSO_2CH(CH_3)_2$, $NHSO_2$(3-pyridyl) or $N[SO_2$(3-pyridyl)$]_2$; $R^{40}$ is H, methyl or 2-hydroxyethyl; $R^{41}$ is methyl optionally substituted with 2-pyridyl or 5-isoxazolin-3-onyl, or ethyl 2-substituted with OH, $CO_2CH_2CH_3$, morpholino or with 1-imidazolidin-2-onyl; or $R^{40}$ and $R^{41}$ together with the nitrogen atom to which they are attached form a (4-$CO_2R^{43}$) piperidino, 5-amino-3-hydroxy-1-pyrazolyl or 4-($NR^{44}$)-1-piperazinyl group; $R^{43}$ is H or ethyl; and $R^{44}$ is H, methyl or 2-hydroxyethyl.

13. A method as defined in claim 12 wherein $R^{35}$ is n-propyl or CN; $R^{37}$ is $SO_2NR^{40}R^{41}$, $NHSO_2CH(CH_3)_2$, $NHSO_2$(3-pyridyl) or $N[SO_2$(3-pyridyl)$]_2$; and $R^{40}$ is H or methyl and $R^{41}$ is methyl, ethyl 2-substituted with $CO_2CH_2CH_3$, morpholino or 1-imidazolidin-2-onyl, or $R^{40}$ and $R^{41}$ together with the nitrogen atom to which they are attached form a (4-$CO_2R^{43}$)piperidino or 4-($NR^{44}$)-1-piperazinyl group.

14. A method as defined in claim 1 wherein in said formula (VII) $R^{45}$ is n-propyl; $R^{46}$ is H or methyl; $R^{47}$ is ethyl or n-propyl; $R^{48}$ is ethyl substituted with $CONR^{49}R^{50}$ or $CO_2R^{51}$, vinyl substituted with $CONR^{49}R^{50}$ or $CO_2R^{51}$, acetyl substituted with $NR^{49}R^{50}$, or $SO_2NR^{49}R^{50}$, or $CONR^{49}R^{50}$, or $CO_2R^{51}$, or bromo; $R^{49}$ and $R^{50}$ together with the nitrogen atom to which they are attached form a morpholino, 4-($NR^{52}$)-1-piperazinyl or 2,4-dimethyl-1-imidazolyl group; $R^{51}$ is H or t-butyl; and $R^{52}$ is methyl or 2-hydroxyethyl.

15. A method as defined in claim 1 wherein in said formula (VIII) $R^{55}$ is H, methyl or ethyl; and $R^{56}$ is $C_1$–$C_6$ alkyl optionally substituted with cyclohexyl or with morpholino.

16. A method as defined in claim 1 wherein in said formula (IX) $R^{57}$ is H, halogen or $C_1$–$C_6$ alkyl.

17. A method as defined in claim 16 wherein $R^{57}$ is H.

18. A method as claimed in claim 16 wherein $R^{57}$ is halogen.

19. A method as defined in claim 18 wherein $R^{57}$ is fluorine.

20. A method as defined in claim 1 wherein in said formula (IX) $R^{58}$ is hydrogen, $C_{1-6}$ alkyl, halo $C_{1-6}$ alkyl, $C_{3-8}$ cycloalkyl, $C_{3-8}$ cycloalkyl $C_{1-3}$ alkyl, aryl $C_{1-3}$ alkyl or heteroaryl $C_{1-3}$ alkyl.

21. A method as defined in claim 1 wherein in said formula (IX) $R^{58}$ is hydrogen, $C_{1-4}$ alkyl, halo $C_{1-4}$ alkyl, $C_{3-6}$ cycloalkyl, $C_{3-6}$ cycloalkylmethyl, pyridyl $C_{1-3}$ alkyl, furyl $C_{1-3}$ alkyl or optionally substituted benzyl.

22. A method as defined in claim 1 wherein in said formula (IX) $R^{58}$ is $C_{1-4}$ alkyl, $C_{3-6}$ cycloalkyl, or $C_{3-6}$ cycloalkylmethyl.

23. A method as defined in claim 21 wherein $R^{58}$ is fluorobenzyl.

24. A method as defined in claim 1 wherein in said formula (IX) $R^{59}$ is an optionally substituted benzene, thiophene, furan, pyridine or naphthalene ring or an optionally substituted bicyclic ring

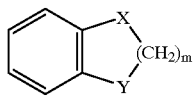

where m is 1 or 2 and X and Y are each $CH_2$ or O.

25. A method as defined in claim 1 wherein in said formula (IX) $R^{59}$ is a benzene ring substituted by $C_{1-3}$ alkoxy, or by $C_{1-3}$ alkoxy and halogen.

26. A method as defined in claim 1 wherein in said formula (IX) $R^{59}$ is 3,4-methylenedioxyphenyl.

27. A method as defined in claim 1 wherein in said formula (IX) $R^{60}$ is hydrogen.

28. A method as defined in claim 1 wherein in said formula (IX) $R^{58}$ and $R^{60}$ together are a 3-membered alkyl chain.

29. A method as defined in claim 1 wherein in said formulae (XA) and (XB) $R^{61}$ is $C_1$–$C_2$ alkyl substituted with $C_3$–$C_5$ cycloalkyl, $CONR^{65}R^{66}$ or a N-linked heterocyclic group selected from pyrazolyl, triazolyl, morpholinyl and 4-$R^{67}$-piperazinyl; $(CH_2)_p$Het or $(CH_2)_q$Ar; $R^{65}$ is H; $R^{66}$ is $C_1$–$C_4$ alkyl optionally substituted with $C_1$–$C_4$ alkoxy, or, $R_{65}$ and $R^{66}$ together with the nitrogen atom to which they are attached, form a morpholinyl group; Het is selected from pyridinyl, 1-oxidopyridinyl, pyridazinyl, pyrimidinyl, pyrazinyl, imidazolyl, isoxazolyl, thiazolyl, triazolyl and oxadiazolyl, any of which is optionally substituted with one or two substituents selected from $CH_3$, $CH_2CH_2OCH_3$, $OCH_3$ and $NH_2$.

30. A method as defined in claim 29 wherein in said formulae (XA) and (XB) $R^{61}$ is $C_1$–$C_2$ alkyl substituted with cyclobutyl, $CONR^{65}R^{66}$, pyrazol-1-yl, 1,2,3-triazol-1-yl, 1,2,4-triazol-1-yl, morpholin-4-yl or 4-methylpiperazin-1-yl; pyrimidin-2-yl; $CH_2$Het or $(CH_2)_q$Ar; $R^{62}$ is $C_1$–$C_3$ alkyl; $R^{63}$ is $C_1$–$C_3$ alkyl optionally substituted with $C_1$–$C_2$ alkoxy; $R^{65}$ is H; $R^{66}$ is $C_1$–$C_2$ alkyl optionally substituted with $C_1$–$C_2$ alkoxy, or $R^{65}$ and $R^{66}$ together with the nitrogen atom to which they are attached, form a morpholin-4-yl group; $R^{70}$ is $C_1$–$C_2$ alkyl optionally monosubstituted with OH, $OCH_3$ or $CONH_2$; Het is selected from pyridin-2-yl, 1-oxidopyridin-2-yl, pyridin-3-yl, pyridazin-3-yl, pyridazin-4-yl, pyrimidin-4-yl, pyrimidin-5-yl, pyrazin-2-yl, 3-methoxypyridin-2-yl, 6-aminopyridin-2-yl, 1-methylimidazol-2-yl, 3,5-dimethylisoxazol-4-yl, 2-methylthiazol-4-yl, 1-methyl-1,2,4-triazol-5-yl, 1-(2-methoxyethyl)-1,2,4-triazol-5-yl, 4-methyl-1,2,4-triazol-3-yl, 3-methyl-1,2,4-triazol-5-yl, 1,2,4-oxadiazol-3-yl and 5-methyl-1,2,4-oxadiazol-3-yl; Ar is selected from phenyl, 4-chlorophenyl, 4-bromophenyl, 2-cyanophenyl, 2-carbamoylphenyl, 4-carbamoylphenyl, 2-nitrophenyl, 4-nitrophenyl, 2-aminophenyl, 4-aminophenyl, 2-methanesulfonamidophenyl, 4-methanesulfonamidophenyl, 4-ethanesulfonamidophenyl, 4-(prop-2-ylsulfonamido)phenyl and 4-sulfamoylphenyl.

31. A method as defined in claim 30 wherein in said formulae (XA) and (XB) $R^{61}$ is cyclobutylmethyl, morpholin-4-ylcarbonylmethyl, 2-(morpholin-4-yl)ethyl, pyrimidin-2-yl, $CH_2$Het or $(CH_2)_q$Ar; $R^{62}$ is $CH_2CH_3$ or $CH_2CH_2CH_3$; $R^{63}$ is $CH_2CH_3$, $CH_2CH_2CH_3$ or $CH_2CH_2OCH_3$; $R^{70}$ is $CH_3$, $CH_2CH_3$ or $CH_2CH_2OH$; Het is selected form pyridin-2-yl, pyridazin-3-yl, pyrazin-2-yl, 3-methoxypyridin-2-yl, 6-aminopyridin-2-yl, 1-methylimidazol-2-yl, 3,5-dimethylisoxazol-4-yl, 1-methyl-1,2,4-triazol-5-yl, 1-(2-methoxyethyl)-1,2,4-triazol-5-yl and 5-methyl-1,2,4-oxadiazol-3-yl; Ar is selected from phenyl, 2-aminophenyl, 2-methanesulfonamidophenyl, 4-methanesulfonamidophenyl, 4-ethanesulfonamidophenyl and 4-(prop-2-ylsulfonamido) phenyl.

32. A method as defined in claim 1 wherein said compound of said formula (I) is selected from:
- 5-[2-allyloxy-5-(4-methylpiperazinylsulfonyl)phenyl]-1-methyl-3-n-propyl-1,6-dihydro-7H-pyrazolo[4,3-d]pyrimidin-7-one,
- 5-[2-ethoxy-5-(piperazinylsulfonyl)phenyl]-1-methyl-3-n-propyl-1,6-dihydro-7H-pyrazolo[4,3-d]pyrimidin-7-one,
- 5-[2-ethoxy-5-(4-methylpiperazinylsulfonyl)phenyl]-1-methyl-3-n-propyl-1,6-dihydro-7H-pyrazolo[4,3-d]pyrimidin-7-one,
- 5-{2-ethoxy-5-[4-(2-propyl)piperazinylsulfonyl]phenyl}-1-methyl-3-n-propyl-1,6-dihydro-7H-pyrazolo[4,3-d]pyrimidin-7-one,
- 5-{2-ethoxy-5-[4-(2-hydroxyethyl)piperazinylsulfonyl]phenyl}-1-methyl-3-n-propyl-1,6-dihydro-7H-pyrazolo[4,3-d]pyrimidin-7-one,
- 1-methyl-5-[5-piperazinylsulfonyl)-2-n-propoxyphenyl]-3-n-propyl-1,6-dihydro-7H-pyrazolo[4,3-d]pyrimidin-7-one,
- 5-{5-[4-(2-hydroxyethyl)piperazinylsulfonyl]-2-n-propoxyphenyl}-1-methyl-3-n-propyl-1,6-dihydro-7H-pyrazolo[4,3-d]pyrimidin-7-one and the pharmaceutically acceptable salts thereof.

33. A method as defined in claim 32 wherein said compound is 5-[2-ethoxy-5-(4-methylpiperazinylsulfonyl)phenyl]-1-methyl-3-n-propyl-1,6-dihydro-7H-pyrazolo[4,3-d]pyrimidin-7-one.

34. A method as defined in claim 33 wherein said compound is a citrate salt of 5-[2-ethoxy-5-(4-methylpiperazinylsulfonyl)phenyl]-1-methyl-3-n-propyl-1,6-dihydro-7H-pyrazolo[4,3-d]pyrimidin-7-one.

35. A method as defined in claim 1 wherein said compound of said formula (II) is selected from:
- 5-[2-ethoxy-5-(1-methyl-2-imidazolyl)phenyl]-1-methyl-3-n-propyl-1,6-dihydro-7H-pyrazolo[4,3-d]pyrimidin-7-one,
- 5-[2-ethoxy-5-(4-methyl-1-piperazinylcarbonyl)phenyl]-1-methyl-3-n-propyl-1,6-dihydro-7H-pyrazolo[4,3-d]pyrimidin-7-one,
- 5-[5-(4-acetyl-1-piperazinyl)acetyl-2-ethoxyphenyl]-1-methyl-3-n-propyl-1,6-dihydro-7H-pyrazolo[4,3-d]pyrimidin-7-one,
- 5-(2-ethoxy-5-morpholinoacetylphenyl)-1-methyl-3-n-propyl-1,6-dihydro-7H-pyrazolo[4,3-d]pyrimidin-7-one,
- 5-(5-morpholinoacetyl-2-propoxyphenyl)-1-methyl-3-n-propyl-1,6-dihydro-7H-pyrazolo[4,3-d]pyrimidin-7-one and the pharmaceutically acceptable salts thereof.

36. A method as defined in claim 1 wherein said compound of said formula (V) is selected from:
- 2-{2-ethoxy-5-[4-(2-hydroxyethyl)-1-piperazinylsulfonyl]phenyl}-8-methylquinazolin-4(3H)-one,
- 2-{5-[4-(2-hydroxyethyl)-1-piperazinylsulfonyl]2-n-propoxyphenyl}-8-methylquinazolin-4(3H)-one,
- 8-methyl-2-{5-[2-(4-methyl-1-piperazinylcarbonyl)ethenyl]-2-n-propoxyphenyl}quinazolin-4(3H)-one,
- 8-carbamoyl-2-{2-ethoxy-5-[4-(2-hydroxyethyl)-1-piperazinylsulfonyl]phenyl}quinazolin-4(3H)-one,
- 8-ethylcarbamoyl-2-(2-n-propoxyphenyl)quinazolin-4(3H)-one and the pharmaceutically acceptable salts thereof.

37. A method as defined in claim 1 wherein said compound of said formula (VI) is selected from:
- 2-[2-ethoxy-5-(4-ethoxycarbonylpiperidinosulfonyl)phenyl]-8-n-propylpyrido[3,2-d]pyrimidin-4(3H)-one,
- 2-[5-(4-carboxypiperidinosulfonyl)-2-ethoxyphenyl]-8-n-propylpyrido[3,2-d]pyrimidin-4(3H)-one,
- 2-{2-ethoxy-5-[4-(2-hydroxyethyl)-1-piperazinylsulfonyl]phenyl}-8-n-propylpyrido[3,2-d]pyrimidin-4(3H)-one,
- 2-{2-ethoxy-5-[(bis-3-pyridylsulfonyl)amino]phenyl}-8-n-propylpyrido[3,2-d]pyrimidin-4(3H)-one and the pharmaceutically acceptable salts thereof.

38. A method as defined in claim 1 wherein said compound of said formula (VII) is selected from:
- 6-(5-bromo-2-n-propoxyphenyl)-3-methyl-1-n-propyl-1,5-dihydro-4H-pyrazolo[3,4-d]pyrimidin-4-one,
- 3-methyl-6-(5-morpholinosulfonyl-2-n-propoxyphenyl)-1-n-propyl-1,5-dihydro-4H-pyrazolo[3,4-d]pyrimidin-4-one,
- 6-[5-(2-carboxyvinyl)-2-n-propoxyphenyl]-3-methyl-1-n-propyl-1,5-dihydro-4H-pyrazolo[3,4-d]pyrimidin-4-one,
- 6-[5-(2-t-butoxycarbonylvinyl)-2-n-propoxyphenyl]-3-methyl-1-n-propyl-1,5-dihydro-4H-pyrazolo[3,4-d]pyrimidin-4-one,
- 3-methyl-6-[5-(2-morpholinocarbonylvinyl)-2-n-propoxyphenyl]-1-n-propyl-1,5-dihydro-4H-pyrazolo[3,4-d]pyrimidin-4-one,
- 3-methyl-6-[5-(2-morpholinocarbonylethyl)-2-n-propoxyphenyl]-1-n-propyl-1,5-dihydro-4H-pyrazolo[3,4-d]pyrimidin-4-one and the pharmaceutically acceptable salts thereof.

39. A method as defined in claim 1 wherein said compound of said formula (VIII) is selected from:
- 5-[2-ethoxy-5-(3-morpholinopropylsulfamoyl)-phenyl]-1,3-dimethyl-1,6-dihydro-7H-pyrazolo[4,3-d]pyrimidin-7-one,
- 1-ethyl-5-[5-(n-hexylsulfamoyl)-2-n-propoxyphenyl]-3-methyl-1,6-dihydro-7H-pyrazolo[4,3-d]pyrimidin-7-one,
- 1-ethyl-5-(5-diethylsulfamoyl-2-n-pro-poxyphenyl)-3-methyl-1,6-dihydro-7H-pyrazolo[4,3-d]pyrimidin-7-one,
- 5-[5-(N-cyclohexylmethyl-N-methylsulfamoyl)-2-n-propoxyphenyl]1-ethyl-3-methyl-1,6-dihydro-7H-pyrazolo[4,3-d]pyrimidin-7-one and the pharmaceutically acceptable salts thereof.

40. A method as defined in claim 1 wherein said compound of said formula (IX) is selected from:
- cis-2,3,6,7,12,12a-hexahydro-2-(4-pyridylmethyl)-6-(3,4-methylenedioxyphenyl)-pyrazino[2',1':6,1]pyrido[3,4-b]indole-1,4-dione,
- cis-2,3,6,7,12,12a-hexahydro-6-(2,3-dihydrobenzo[b]furan-5-yl)-2-methyl-pyrazino[2',1':6,1]pyrido[3,4-b]indole-1,4-dione,
- cis-2,3,6,7,12,12a-hexahydro-6-(5-bromo-2-thienyl)-2-methyl-pyrazino[2',1':6,1]pyrido[3,4-b]indole-1,4-dione,
- cis-2,3,6,7,12,12a-hexahydro-2-butyl-6-(4-methylphenyl)pyrazino[2',1':6,1]pyrido[3,4-b]indole-1,4-dione,
- cis-2,3,6,7,12,12a-hexahydro-2-cyclopropyl-6-(3,4-methylenedioxyphenyl)-pyrazino[2',1':6,1]pyrido[3,4-b]indole-1,4-dione, (3S,6R,12aR)-2,3,6,7,12,12a-hexahydro-3-methyl-6-(3, 4-methylenedioxyphenyl)-pyrazino[2',1':6,1]pyrido[3, 4-b]indole-1,4-dione, (3S,6R,12aR)-2,3,6,7,12,12a-hexahydro-2,3-dimethyl-6-(3,4-methylenedioxyphenyl)-pyrazino[2',1':6,1]pyrido[3,4-b]indole-1,4-dione, (6R,12aR)-2,3,6,7,12,12a-hexahydro-2-isopropyl-6-(3,4-methylenedioxyphenyl)-pyrazino[2',1':6,1]pyrido[3,4-b]indole-1,4-dione, (6R,12aR)-2,3,6,7,12,12a-hexahydro-2-cyclopentyl-6-(3, 4-methylenedioxy phenyl)-pyrazino[2',1':6,1]pyrido[3, 4-b]indole-1,4-dione, (6R,12aR)-2,3,6,7,12,12a-hexahydro-2-cyclopropylmethyl-6-(4-methoxyphenyl)-pyrazino[2', 1':6,1]pyrido[3,4-b]indole-1,4-dione, (6R,12aR)-2,3,6,7,12,12a-hexahydro-6-(3-chloro-4-methoxyphenyl)-2-methyl-pyrazino[2',1':6,1]pyrido[3, 4-b]indole-1,4-dione, (6R,12aR)-2,3,6,7,12,12a-hexahydro-2-methyl-6-(3,4-methylenedioxyphenyl)-pyrazino[2',1':6,1]pyrido[3,4-b]indole-1,4-dione, (6R,12aR)-2,3,6,7,12,12a-hexahydro-6-(3,4-methylenedioxyphenyl)-pyrazino[2',1':6,1]pyrido[3,4-b]indole-1,4-dione, (5aR,12R,14aS)-1,2,3,5,6,11,12,14a-octahydro-12-(3,4-methylenedioxyphenyl)-pyrrolo[1",2":4',5']pyrazino[2',1':6,1]pyrido[3,4-b]indole-5-1,4-dione, and the pharmaceutically acceptable salts thereof.

41. A method as defined in claim 1 wherein said compound of said formulae (XA) or (XB) is selected from:

5-{5-[4-(2-hydroxyethyl)piperazin-1-ylsulfonyl]-2-n-propoxyphenyl}-3-n-propyl-1-(pyridin-2-yl)methyl-1, 6-dihydro-7H-pyrazolo[4,3-d]pyrimidin-7-one, 1-(1-methylimidazol-2-yl)methyl-5-[5-(4-methylpiperazin-1-ylsulfonyl)-2-n-propoxyphenyl]-3-n-propyl-1,6-dihydro-7H-pyrazolo[4,3-d]pyrimidin-7-one, 5-{5-[4-(2-hydroxyethyl)piperazin-1-ylsulfonyl]-2-n-propoxyphenyl}-3-n-propyl-2-(pyridin-2-yl)methyl-2, 6-dihydro-7H-pyrazolo[4,3-d]pyrimidin-7-one, 5-[5-(4-ethylpiperazin-1-ylsulfonyl)-2-n-propoxyphenyl]-3-n-propyl-2-(pyridin-2-yl)methyl-2, 6-dihydro-7H-pyrazolo[4,3-d]pyrimidin-7-one, 3-ethyl-5-[5-(4-ethylpiperazin-1-ylsulfonyl)-2-n-propoxyphenyl]-2-(pyridin-2-yl)methyl-2,6-dihydro-7H-pyrazolo[4,3-d]pyrimidin-7-one, 5-[5-(4-ethylpiperazin-1-ylsulfonyl)-2-n-propoxyphenyl]-3-n-propyl-2-(pyridazin-3-yl)methyl-2,6-dihydro-7H-pyrazolo[4,3-d]pyrmidin-7-one, 5-[5-(4-ethylpiperazin-1-ylsulfonyl)-2-n-propoxyphenyl]-3-n-propyl-2-(pyridazin-2-yl)methyl-2,6-dihydro-7H-pyrazolo[4,3-d]pyrimidin-7-one, 5-[2-ethoxy-5-(4-ethylpiperazin-1-ylsulfonyl)phenyl]-3-n-propyl-2-(pyridin-2-yl)methyl-2,6-dihydro-7H-pyrazolo[4,3-d]pyrimidin-7-one, and the pharmaceutically acceptable salts thereof.

42. A method of preventing nitrate-induced tolerance in a mammal comprising administering to said mammal a nitrate-induced tolerance preventing amount of a cGMP PDE inhibitor.

* * * * *